(12) United States Patent
Wise et al.

(10) Patent No.: US 7,144,995 B2
(45) Date of Patent: Dec. 5, 2006

(54) FLUORESCENT NITROGENOUS BASE AND NUCLEOSIDES INCORPORATING SAME

(75) Inventors: Dean S. Wise, Ann Arbor, MI (US); Anthony D. Sercel, Ann Arbor, MI (US); Kee-Yong Jung, Ann Arbor, MI (US); David A. Berry, Ann Arbor, MI (US); John B. Randolph, Great Falls, VA (US); Robert L. Somers, Rockville, MD (US); Hugh Mackie, Round Hill, VA (US)

(73) Assignees: Glen Research Corporation, Sterling, VA (US); Berry & Associates, Dexter, MI (US)

( * ) Notice: Subject to any disclaimer, the term of this patent is extended or adjusted under 35 U.S.C. 154(b) by 453 days.

(21) Appl. No.: 10/382,754

(22) Filed: Mar. 6, 2003

(65) Prior Publication Data

US 2004/0009933 A1 Jan. 15, 2004

Related U.S. Application Data

(60) Provisional application No. 60/362,448, filed on Mar. 8, 2002.

(51) Int. Cl.
*C07G 3/00* (2006.01)
*C07H 21/00* (2006.01)
*C12Q 1/68* (2006.01)

(52) U.S. Cl. ............ 536/4.1; 536/1.11; 536/23.1; 536/24.3; 435/6

(58) Field of Classification Search .......... 536/1.11, 536/4.1, 23.1, 24.3; 435/6
See application file for complete search history.

(56) References Cited

U.S. PATENT DOCUMENTS

| | | | |
|---|---|---|---|
| 5,144,019 A | 9/1992 | Rossi et al. | 536/27 |
| 5,225,337 A | 7/1993 | Robertson et al. | 435/91 |
| 5,582,981 A | 12/1996 | Toole et al. | 435/6 |
| 5,756,291 A | 5/1998 | Griffin et al. | 435/6 |
| 5,840,867 A | 11/1998 | Toole et al. | 536/23.1 |
| 6,458,559 B1 | 10/2002 | Shi et al. | 435/69.1 |
| 6,475,998 B1 | 11/2002 | Soreq et al. | 514/44 |
| 6,509,460 B1 | 1/2003 | Beigelman et al. | 536/26.26 |
| 6,511,809 B1 | 1/2003 | Baez et al. | 435/6 |
| 6,515,120 B1 | 2/2003 | Kwagh et al. | 536/25.4 |
| 6,524,853 B1 | 2/2003 | Kohara et al. | 435/325 |

FOREIGN PATENT DOCUMENTS

| | | |
|---|---|---|
| JP | 62-59293 | 3/1987 |
| JP | 62-255499 | * 11/1987 |
| WO | WO 98/49177 | 11/1998 |
| WO | WO 99/06422 | 2/1999 |

OTHER PUBLICATIONS

Corey et al., "Locked Nucleic Acid (LNA): Fine-Tuning the Recognization of DNA and RNA," Chemistry & Biology, 8 pp. 1-7, (2001).

(Continued)

*Primary Examiner*—Jezia Riley
(74) *Attorney, Agent, or Firm*—Banner & Witcoff, Ltd.

(57) ABSTRACT

A fluorescent nitrogenous base and nucleosides including the fluorescent nitrogenous base are provided. Nucleosides including the fluorescent nitrogenous base are capable of Watson-Crick base pairing with naturally occurring nucleosides. The nucleosides including the fluorescent nitrogenous base have many uses including but not limited to use in probes, in the synthesis of nucleic acids, and in investigating nucleic acid interactions with other nucleic acids and/or with proteins.

3 Claims, 10 Drawing Sheets

OTHER PUBLICATIONS

Barrio et al., "Fluorescent Cytidine Derivatives," Biochemical and Biophysical Research Communications, vol. 46, No. 2, (1972).

Cairns et al., "Target Site Selection for an RNA-Cleaving Catalytic DNA," Nature Biotechnology, vol. 17, (1999).

Ellington et al., "In Vitro Selection of RNA Molecules that Bind Specific Ligands," Nature, vol. 346, (1990).

Freier et al., "The Ups and Downs of Nucleic Acid Duplex Stability: Structure-Stability Studies on Chemically-Modified DNA:RNA Duplexes," Nucleic Acids Research, vol. 25, No. 22 pp. 4429-4443, (1997).

Sergei M. Gryaznov, "Oligonucleotide N3'→P5' Phosphoramidates as Potential Therapeutic Agents," Biochimica et Biophysica Acta 1489; 131-140, (1999).

Hawkins et al., "Incorporation of a Fluorescent Guanosine Analog Into Oligonucleotides and its Application to a Real Time Assay for the HIV-1 Integrase 3'Processing Reaction," Nucleic Acids Research, vol. 23, No. 15, pp. 2872-2880, (1995).

Morita et al., "2'-0, 4'-C-Ethylene-Bridged Nucleic Acids (ENA): High Nuclease-Resistant and Thermodynamically Stable Oligonucleotides for Antisense Drug," Bioorganic & Medicinal Chemistry Letters vol. 12, pp. 73-76 (2002).

James et al., "The Secondary Structure of Ribonuclease P. RNA, The Catalytic Element of a Ribonucleoprotein Enzyme," Cell, vol. 52, pp. 19-26, (1988).

Gerald F. Joyce, "Nucleic Acid Enzymes: Playing with a Fuller Deck," The National Academy of Sciences, vol. 95, pp. 5845-5847, (1988).

Hesselberth et al., "In Vitro Selection of Nucleic Acids for Diagnostics Applications," Molecular Biotechnology, vol. 74, pp. 15-25, (2000).

Landegren, et al. "DNA Diagnostics-Molecular Techniques and Automation," Science, vol. 242.

Lund et al., "Phase II Study of Gemcitabine (2',2'-Difluorodeoxycytidine) in Previously Treated Ovarian Cancer Patients," Journal of the National Cancer Institute, vol. 86, No. 20 (1994).

McGuigan et al., "Anti-Varicella-Zoster Virus Bicyclic Nucleosides: Replacement of Furo by Pyrro Base Reduces Antiviral Potency", Antiviral Chemistry & Chemotherapy, vol. 11, pp. 343-348.

McGuigan et al., "Potent and Selective Inhibition of Varicella-Zoster Virus (VZV) by Nucleoside Analogues with an Unusual Bicyclic Base," American Chemical Society, vol. 42, pp. 4479-4484, (1999).

Jason Micklefield, "Backbone Modification of Nucleic Acids: Synthesis, Structure and Therapeutic Applications," Current Medicinal Chemistry, vol. 8, pp. 1157-1179, (2001).

Tuerk et al., "Systematic Evolution of Ligands by Exponential Enrichment: RNA Ligands to Bacteriophage T4 DNA Polymerase," Science, vol. 249, (1990).

Tarasow et al., "RNA-Catalysed Carbon-Carbon Bond Formation," Nature, vol. 389 (1997).

Sood et al., "Boron-Containing Nucleic Acids 2.[1] Synthesis of Oligodeoxynucleoside Boronophosphates," American Chemical Society, (1990).

Robins et al., "Nucleic Acid Related Compounds. 39. Efficient Conversion of 5-Iodo to 5-Alkynyl and Derived 5-Substituted Uracil Bases and Nucleosides[1]," American Chemical Society, vol. 48, pp. 1854-1862 (1983).

Reader et al., "A Ribozyme Composed of Only Two Different Nucleotides", Nature, vol. 420, (2002).

Ray, et al., "Peptide Nucleic Acid (PNA) Its Medical and Biotechnical Applications and Promise for the Future," The FASEB Journal, vol. 14, (2000).

Rait et al., "Boranophosphate Nucleic Acids-A Versatile DNA BackBone," Nucleosides & Nycleotides vol. 18, pp. 1379-1380 (1999).

Morris et al., "Enrichment for RNA Molecules that Bind a Diels-Alder Transition State Analog," Proc. Natl. Acad. Sci. USA, vol. 91, pp. 1302-13032, (1994).

Cuihua Liu et al., "Fluorescence Characterization of the Transcription Bubble in Elongation Complexes ofT7 RNA Polymerase", JMB, vol. 308, pp. 465-475, (2001).

John M. jean et al., "2-Aminopurine Fluorescence Quenching and Lifetimes: Role of Base Stacking"; PNAS, vol. 98; pp. 37-41, (2001).

Jinsuk Woo et al., "G/C-modified Oligodeoxynucleotides with Selective Complementarity: Synthesis and Hybridization Properties", Nucleic Acids Research, vol. 24, No. 13, pp. 2470-2475, (1996).

Susan M. Freier et al., "The Ups and Downs of Nucleic Acid Duplex Stability: Structure-Stability Studies on Chemically-Modified DNA: RNA Duplexes", Nucleic Acids Research, Vo. 25, No. 22, pp. 4429-4443, (1997).

James M. Prober et al., "A System for Rapid DNA Sequencing with Fluorescent Chain-Terminating Dideoxynucleotides", Science, vol. 238, pp. 336-341, (1987).

Suresh C. Srivastava et al., "$N^6$-Etheno Deoxy and Ribo Adenosine and $3,N^4$-Etheno Deoxy and Ribo Cytidine Phosphoramidites. Strongly Fluorescent Structures for Selective Introduction in Defined Sequence DNA and RNA Molecules", Nucleic Acid Research, vol. 22, No. 7, pp. 1296-1304, (1994).

Mary E. Hawkins et al., "Incorporation of a Fluorescent Guanosine Analog Into Oligonucleotides and its Application to a Real Time Assay for the HIV-1 Integrase 3'Processing Reaction", Nucleid Acids Research, vol. 23, No. 15, pp. 2872-2880, (1995).

C. McGuidan et al., "Anti-varicella-zoster Virus Bicyclic Nucleosides: Replacement of Furo by Pyrro Base Reduces Antiviral Potency", Antiviral Chemistry & Chemotherapy, vol. 11, pp. 343-348.

Jorge R. Barrio, "Fluorescent Adenosine and Cytidine Derivatives", Biochemialand biophysical Research Communications, vol. 46, No. 2, (1972).

Ulf Landegren et al., "DNA diagnostics-Molecular Techniques and Automation", Science, Vo. 242, pp. 229-237.

Mary E. Hawkins et al., "Fluorescene Properties of Pteridine Nucleoside Analogs as Monomers and Incorporated into Oligonucleotides", Analytical Biochemistry vol. 244, pp. 86-95 (1997).

Sarah L. Driscoll et al., "Fluorescene Properties of a New Guanosine Analog Incorporated into Small Oligonucleotides", Biophysical Journal, vol. 73, pp. 3277-3286 (1997).

Hawkins, et al. "Synthesis and Fluorescence Characterization of Pteridine Adenosine Nucleoside Analogs for DNS Incorporation", Analytical Biochemistry vol. 298, 231-240 (2001).

* cited by examiner

SEQUENCE LISTING

<160> NUMBER OF SEQ ID NOS: 10

<210> SEQ ID NO 1
<211> LENGTH: 18
<212> TYPE: DNA
<213> ORGANISM: artificial sequence
<220> FEATURE:
<223> OTHER INFORMATION: chemically synthesized sequence
<220> FEATURE:
<221> NAME/KEY: misc_feature
<222> LOCATION: (11)..(11)
<223> OTHER INFORMATION: n is pyrrolo-dC

<400> SEQUENCE: 1
gcctaacttc nggagatg                                                        18

<210> SEQ ID NO 2
<211> LENGTH: 3
<212> TYPE: RNA
<213> ORGANISM: artificial sequence
<220> FEATURE:
<223> OTHER INFORMATION: miscellaneous RNA sequence
<220> FEATURE:
<221> NAME/KEY: misc_feature
<222> LOCATION: (2)..(2)
<223> OTHER INFORMATION: n is pyrrolo-C

<400> SEQUENCE: 2 cnc                                                                         3

<210> SEQ ID NO 3
<211> LENGTH: 6
<212> TYPE: DNA
<213> ORGANISM: Homo sapiens

<400> SEQUENCE: 3 ttaggg                                                                      6

<210> SEQ ID NO 4
<211> LENGTH: 6
<212> TYPE: DNA
<213> ORGANISM: Homo sapiens

<400> SEQUENCE: 4 aatccc                                                                      6

<210> SEQ ID NO 5
<211> LENGTH: 6
<212> TYPE: DNA
<213> ORGANISM: artificial sequence
<220> FEATURE:
<223> OTHER INFORMATION: miscellaneous DNA sequence that can bind to
    telomerase sequence
<220> FEATURE:
<221> NAME/KEY: misc_feature

```
<222> LOCATION: (4)..(6)
<223> OTHER INFORMATION: n is pyrrolo-dC

<400> SEQUENCE: 5 aatnnn                                                                    6

<210> SEQ ID NO 6
<211> LENGTH: 19
<212> TYPE: DNA
<213> ORGANISM: artificial sequence
<220> FEATURE:
<223> OTHER INFORMATION: artificial primer sequence
<220> FEATURE:
<221> NAME/KEY: misc_feature
<222> LOCATION: (9)..(9)
<223> OTHER INFORMATION: n is pyrrolo-dC

<400> SEQUENCE: 6
taatacgant cactatagg                                                     19

<210> SEQ ID NO 7
<211> LENGTH: 19
<212> TYPE: DNA
<213> ORGANISM: artificial sequence
<220> FEATURE:
<223> OTHER INFORMATION: artificial primer sequence
<220> FEATURE:
<221> NAME/KEY: misc_feature
<222> LOCATION: (9)..(9)
<223> OTHER INFORMATION: n is pyrrolo-dC
<220> FEATURE:
<221> NAME/KEY: misc_feature
<222> LOCATION: (11)..(11)
<223> OTHER INFORMATION: n is pyrrolo-dC

<400> SEQUENCE: 7
taatacgant nactatagg                                                     19

<210> SEQ ID NO 8
<211> LENGTH: 19
<212> TYPE: DNA
<213> ORGANISM: artificial sequence
<220> FEATURE:
<223> OTHER INFORMATION: artificial primer sequence
<220> FEATURE:
<221> NAME/KEY: misc_feature
<222> LOCATION: (6)..(6)
<223> OTHER INFORMATION: n is pyrrolo-dC
<220> FEATURE:
<221> NAME/KEY: misc_feature
<222> LOCATION: (9)..(9)
<223> OTHER INFORMATION: n is pyrrolo-dC
<220> FEATURE:
<221> NAME/KEY: misc_feature
<222> LOCATION: (11)..(11)
<223> OTHER INFORMATION: n is pyrrolo-dC

<400> SEQUENCE: 8
taatangant nactatagg                                                     19

<210> SEQ ID NO 9
<211> LENGTH: 19
<212> TYPE: DNA
<213> ORGANISM: artificial sequence
<220> FEATURE:
<223> OTHER INFORMATION: artificial primer sequence
<220> FEATURE:
<221> NAME/KEY: misc_feature
<222> LOCATION: (6)..(6)
<223> OTHER INFORMATION: n is pyrrolo-dC
<220> FEATURE:
```

```
<221> NAME/KEY: misc_feature
<222> LOCATION: (9)..(9)
<223> OTHER INFORMATION: n is pyrrolo-dC
<220> FEATURE:
<221> NAME/KEY: misc_feature
<222> LOCATION: (11)..(11)
<223> OTHER INFORMATION: n is pyrrolo-dC
<220> FEATURE:
<221> NAME/KEY: misc_feature
<222> LOCATION: (13)..(13)
<223> OTHER INFORMATION: n is pyrrolo-dC

<400> SEQUENCE: 9
taatangant nantatagg                                               19

<210> SEQ ID NO 10
<211> LENGTH: 19
<212> TYPE: DNA
<213> ORGANISM: artificial sequence
<220> FEATURE:
<223> OTHER INFORMATION: artificial primer sequence

<400> SEQUENCE: 10
taatacgact cactatagg                                               19
```

FLUORESCENT NITROGENOUS BASE AND NUCLEOSIDES INCORPORATING SAME

PRIORITY APPLICATION

This application claims the benefit of U.S. Provisional Application No. 60/362,448 filed on 8 Mar. 2002 and entitled "Pyrrolo-dC: A Novel Fluorescent Nucleoside." This priority application is hereby incorporated by reference in its entirety.

FIELD OF THE INVENTION

The present invention is directed to a novel fluorescent nitrogenous base. Some specific examples are directed to nucleosides including a novel fluorescent nitrogenous base possessing properties that allow it to substitute for naturally occurring nitrogenous bases.

BACKGROUND

Nucleosides typically include a nitrogenous base, such as adenine, cytosine, thymine, guanine or uracil, and a sugar moiety, such as ribose or deoxyribose. The sugar moiety can be linked to one or more phosphoryl groups to form a nucleoside phosphate. The nucleoside phosphates can be linked to each other, e.g., through phosphodiester bonds, to form strands of linked nucleoside phosphates. Researchers have long desired fluorescent nucleosides to probe nucleic acid structure. Fluorescent nucleoside bases also would be useful in the analysis of nucleic acid-protein interactions.

It is an object of the present invention to provide a novel fluorescent nitrogenous base that possesses properties that allow it to substitute for at least one of the naturally occurring nitrogenous bases. It is a particular object of at least some examples of the invention to provide a fluorescent nucleoside that possesses properties that allow it to substitute for cytidine. Additional objects and aspects of the invention will be apparent from the following disclosure.

SUMMARY

In accordance with one aspect, a composition of formula (I) is provided:

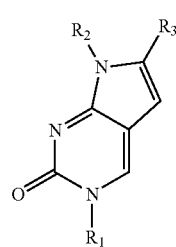

(I)

in which $R_1$ represents hydrogen, a sugar moiety, a 2',2'-difluoro-2'-deoxyribosyl group, a 5'-(phosphoryloxy)ribosyl group, a 5'-(diphosphoryloxy)ribosyl group, a 5'-(triphosphoryloxy)ribosyl group, a 2'-deoxyribosyl group, a 5'-phosphoryloxy-2'-deoxyribosyl group, a 5'-diphosphoryloxy-2'-deoxyribosyl group, and a 5'-triphosphoryloxy-2'-deoxyribosyl group. $R_1$ may also represent a saturated or unsaturated hydrocarbon group, an aralkyl group, a cycloalkyl group, an aryl group, a heteroaryl group, or a saturated or partially saturated heterocyclic group, wherein any of these groups may be unsubstituted or substituted with one or more substituents, which are the same or different, selected from the group consisting of $R^7$, $OR^7$, $SR^7$, $NR^8COR^7$, $NR^8CSR^7$, $NR^8CO_2R^7$, $NR^8C(O)SR^7$, $NR^8CS_2R^7$, $O_2CR_7$, $S_2CR^7$, $SCOR^7$, $OCSR^7$, $SO_2R^7$, $OSO_2R^7$, $NR^8SO_2R^7$, $CN$, $NO_2$, $N_3$, and a halogen, wherein $R^7$ is an alkyl, an aryl, an aralkyl, wherein $R^7$ is unsubstituted or substituted with one or more halogen atoms, which are the same or different, and $R_8$ is hydrogen or an alkyl. $R_2$ typically represents hydrogen, an acetyl group, or a group that is cleavable or hydrolyzable to yield a hydrogen or an acetyl group. $R_3$ represents hydrogen or a saturated or unsaturated hydrocarbon group having one to eight carbons. One specific composition of formula (I) is referred to below as "pyrrolopyrimidine-C." Pyrrolopyrimidine-C possesses suitable properties such that it can substitute, e.g., functionally substitute, for the base cytosine in any application where cytosine might be used. Pyrrolopyrimidine-C is especially useful as a nitrogenous base in nucleosides, e.g., pyrrolopyrimidine-C can be linked to ribose or deoxyribose, or in nucleoside mono-, di-, and triphosphates.

It is a significant advantage that at least some of the fluorescent nitrogenous bases disclosed herein can substitute for cytosine without substantially altering the properties of nucleosides in which cytosine would normally be present. That is, replacement of cytosine with pyrrolopyrimidine-C does not substantially affect the functioning of the nucleoside in any substantial manner. Thus, replacement of cytosine with pyrrolopyrimidine-C is not believed to substantially alter the structure, e.g., secondary, tertiary or other structure, of any nucleic acid strand which substitutes one or more cytosines with one or more pyrrolopyrimidine-C molecules. Such properties provide for the ability to use pyrrolopyrimidine-C in place of cytosine in many applications, such as in nucleic acid strands, primers, probes, hybridization assays, investigation of nucleic acid-nucleic acid interaction, investigation of nucleic acid-protein interactions, investigation of nucleoside-protein interactions, for therapeutic uses, and the like. Other uses for pyrrolopyrimidine-C will be readily apparent to a person of ordinary skill in the art given the benefit of this disclosure.

In accordance with a second aspect, a composition of formula (II) is provided:

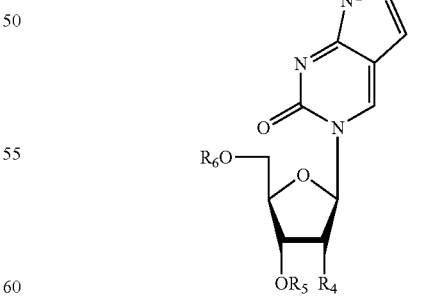

(II)

in which $R_2$ represents hydrogen, an acetyl group, or a group which is cleavable or hydrolyzable to provide a hydrogen or acetyl group. $R_3$ represents a hydrogen or a saturated or unsaturated hydrocarbon having one to eight carbons. $R_4$ represents hydrogen, a hydroxyl group, a protected hydroxyl group, fluorine, an allyloxy group, an alkynylalkoxy group, an aminoalkoxy group, an aminoalkoxy group wherein the amino group bears a protecting group, or a methoxy group. $R_5$ represents hydrogen, an acetyl group, a phosphoryl group, a nucleoside phosphoryl group, a nucleoside thiophosphoryl group, an alkoxy-N,N-dialkylaminophosphinyl group (e.g., a 2-cyanoethoxy-N,N-diisopropylaminophosphinyl group or a methoxy-N,N-diisopropylaminophosphinyl group). $R_6$ represents hydrogen, a phosphoryl group, a diphosphoryl (pyrophosphoryl) group, a triphosphoryl group, a nucleoside phosphoryl group, a nucleoside thiophosphoryl group, a polynuclotidyl group, a dimethoxytrityl group, or a protecting group removable under acidic, neutral, or photochemical conditions. Compositions in accordance with formula (II) in which $R_4$ represents OH are referred to below as "pyrrolo-C." Compositions in accordance with formula (II) in which $R_4$ represents H are referred to below as "pyrrolo-dC." Compositions in accordance with formula (II), e.g., a nucleobase 6-methylpyrrolo[2,3-d]pyrimidine riboside or 2'-deoxyriboside as its phosphoramidite derivative, can be site-specifically incorporated into an oligonucleotide strand through a 3',5'-phosphodiester linkage using an automated oligonucleotide synthesizer or other methods described in more detail below or known to those skilled in the art. Alternatively, various 5'-phosphate derivatives of a nucleobase 6-methylpyrrolo[2,3-d]pyrimidine riboside or 2'-deoxyriboside may be incorporated into an oligonucleotide strand through a 3',5'-phosphodiester linkage using polymerase enzymes as described in more detail below or using methods which will be readily selected by those skilled in the art given the benefit of this disclosure.

An additional aspect relates to a probe comprising at least one nucleoside in which the nitrogenous base of at least nucleoside is pyrrolopyrimidine-C, as shown in formula (I) and/or at least one nucleoside in accordance with the composition of formula (II). The probe is operative to hybridize to a complementary nucleotide, such as a nucleotide comprised of guanosine, or polynucleotide as the case may be. That is, pyrrolopyrimidine-C is capable of Watson-Crick base pairing with a nitrogenous base of another nucleotide such as the guanine base found in a guanosine unit, e.g., pyrrolopyrimidine-C can form three hydrogen bonds to guanine in a fashion analogous to that found when the pyrimidine base of cytidine hydrogen bonds to the purine base of guanosine. Probes comprising a nucleoside in which pyrrolopyrimidine-C is the nitrogenous base may be flanked by one or more additional nucleosides, e.g., as a unit of an oligonucleotide. The additional nucleosides may include any of the naturally occurring nitrogenous bases and/or naturally occurring derivatives thereof, e.g., adenine, guanine, thymine, uracil, cytosine, hypoxanthine, xanthine, uric acid, 4-thiouridine, inosine, 1-methylguanosine, $N^6$-isopentyladenosine, ribothymidine, psuedouridine, dihydrouridine, etc. (in either the keto, enol or other forms if possible), or may include pyrrolopyrimidine-C. One skilled in the art, given the benefit of this disclosure, will be able to select and design suitable probes comprising nucleosides in which pyrrolopyrimidine-C is the nitrogenous base.

In accordance with an additional aspect, an isolated and purified polynucleotide comprising a plurality of nucleosides in which at least one nucleoside includes a nitrogenous base having a composition in accordance with formula (I), and/or at least one nucleoside having a composition in accordance with formula (II), is provided. The isolated polynucleotide may include any number of nucleosides, e.g., two or more linked nucleosides, but typically the isolated polynucleotide comprises between about 2 and about 10000 nucleosides, more preferably between about 5 and about 5000 nucleosides and most preferably between about 10 and about 1000 nucleosides, e.g., between about 15 and about 50 nucleosides. The polynucleotide may be either single stranded or double stranded and may be linear, circular, supercoiled or take other forms.

Additional aspects relate to a vector comprising at least one nucleoside in which the nitrogenous base of the at least one nucleoside has a composition in accordance with formula (I), and/or in which the composition of the at least one nucleoside has a composition in accordance with formula (II). The vector may be linear, circular, or take other forms, and it may be a vector that is capable of insertion into bacterial cells, viral cells, or the like. In accordance with other aspects, a host cell comprising the vector described above is also provided. In accordance with yet other aspects, one or more proteins may be expressed using the host cell comprising the vector described above.

In accordance with additional aspects, a kit for producing a polynucleotide comprising free nucleoside triphosphates and at least one polymerase is provided. The free nucleoside triphosphates include at least one nucleoside that includes a nitrogenous base having the composition of formula (I) and/or at least one nucleoside having the composition of formula (II). The kit may also include other free nucleoside phosphates, such as dATP, dGTP, dTTP, dCTP, dUTP and the like. The polymerase may be any polymerase that is capable of joining, replicating, and/or amplifying nucleic acids including but not limited to Taq polymerase, Pfu polymerase, Vent polymerase, or AmpiTaq polymerase.

Another aspect relates to a method of producing a composition having formula (I) or formula (II). The method generally includes providing a suitable compound capable of forming a nitrogenous base in accordance with formula (I) or a nucleoside in accordance with formula (II). Typically, ring closure of the suitable compound is performed under suitable conditions followed by treatment with ammonia to provide a compound including formula (I) or formula (II). One skilled in the art given the benefit of this disclosure will be able to design and select suitable synthetic methods for forming compounds in accordance with formula (I) or formula (II), using the methods described here and other methods known to those skilled in the art.

Aspects also relate to a method of producing a probe and/or a polynucleotide including at least one nucleoside in which the at least one nucleoside comprises a nitrogenous base having the composition of formula (I) and/or at least one nucleoside having the composition of formula (II) is provided. Typically, the probe can be produced by synthesis, e.g., chemical synthesis of a probe or synthesis using polymerase chain reaction (PCR), or can be produced by insertion of a suitable sequence into a vector and/or host cell system for amplification of the probe sequence. In accordance with certain aspects, the probe may comprise a nucleotide sequence in which some or all of the nitrogenous bases comprise a composition in accordance with formula (I). The probe can be isolated and purified using suitable analytical techniques, such as chromatography, centrifugation, and the like. One skilled in the art given the benefit of this disclosure will be able to design, produce and isolate probes for an intended use.

In accordance with yet other aspects, methods of using a composition comprising formula (I) or formula (II) in a hybridization assay, to investigate nucleic acid-nucleic acid interactions and nucleic acid-protein interactions are provided. The method includes providing a nucleic acid strand in which one or more of the nitrogenous bases of the nucleic acid strand have a composition in accordance with formula (I) or in which one or more nucleosides of the nucleic acid strand have a composition in accordance with formula (II). The nucleic acid strand is allowed to interact with another nucleic acid strand or protein. Suitable conditions will be readily selected by those skilled in the art given the benefit of this disclosure. As discussed more extensively below, because fluorescence emissions of compositions having formula (I) or formula (II) are believed to be sensitive to the local environment, the fluorescence of the nucleic acid strand may change when the strand interacts with another nucleic acid strand or protein. Such changes in fluorescence can provide valuable information about the structure of the nucleic acid duplex or nucleic acid-protein complex. Other fluorescence parameters, such as fluorescence lifetimes, fluorescence quantum yields, fluorescence rate constants, etc., may also change upon hybridization of a nucleic acid strand to another nucleic acid strand or to a protein or amino acid. One skilled in the art, given the benefit of this disclosure, will be able to use nucleic acid strands having compositions in accordance with formula (I) or formula (II) for investigating these and other interactions.

Still another aspect relates to a method of administering a therapeutic amount of a composition including formula (I) or formula (II). As discussed more extensively below, because a nitrogenous base in accordance with formula (I) is recognized by transcriptional proteins (and translational proteins and factors, e.g., ribosomes, enzymes and the like) as cytosine, the nitrogenous base is believed to be capable of substituting for cytosine in numerous applications, e.g., administration of the nitrogenous base can elicit similar effects as cytosine. One skilled in the art given the benefit of this disclosure will be able to treat selected disorders by administration of compositions in accordance with formula (I) or formula (II).

In accordance with yet another aspect, a method of administering a gene in which the gene includes at least one nucleoside having a nitrogenous base in accordance with formula (I) or at least one nucleoside with a composition in accordance with formula (II) is provided. As discussed more extensively below, because replacement of cytosine with a composition in accordance with formula (I) does not substantially alter the function of the nucleoside, e.g., the nucleoside is still recognized as cytosine during transcription, genes comprising nucleosides including compositions in accordance with formula (I) or (II) are still operative to produce functional proteins. By providing a gene comprising a nucleoside including a composition in accordance with formula (I) or (II), in addition to providing a vehicle for producing a desired protein, efficiency of gene delivery may be evaluated, for example. One skilled in the art, given the benefit of this disclosure will be able to select and design genes comprising compositions in accordance with formula (I) or formula (II).

Other aspects relate to the use of compositions having formula (I) and/or formula (II) in aptamers or ribozymes. Such aptamers and ribozymes can provide details about the protein structure, can aid in design of drugs that can bind to proteins, and can be used as diagnostic agents, for example.

The novel fluorescent nitrogenous bases, nucleosides including the novel fluorescent nitrogenous bases, and methods for producing and using them will be recognized by those skilled in the art to represent a significant technological advance. Additional features, advantages, and uses will be understood from the following detailed description of certain examples.

BRIEF DESCRIPTION OF DRAWINGS

Numerous examples are described below with reference to the accompanying drawings, in which:

FIG. 7 is a first gel showing PCR products of pyrrolo-dC substituted and unsubstituted nucleotides where Lane 1 is Standards, Lane 2 is Control (200 µM dCTP), and Lane 3 is 200 µM pyrrolo-dCTP. FIG. 8 is a second gel showing PCR products of pyrrolo-dC substituted and unsubstituted nucleotides where Lanes 1&6 are each standards, Lanes 2 and 4 are each Control (200 µM dCTP), Lanes 3 and 5 are each 200 µM pyrrolo-dCTP. Note standards bottom band is 500 bp and the band immediately above the 500 bp band is a 1000 bp band.

Figure 1:
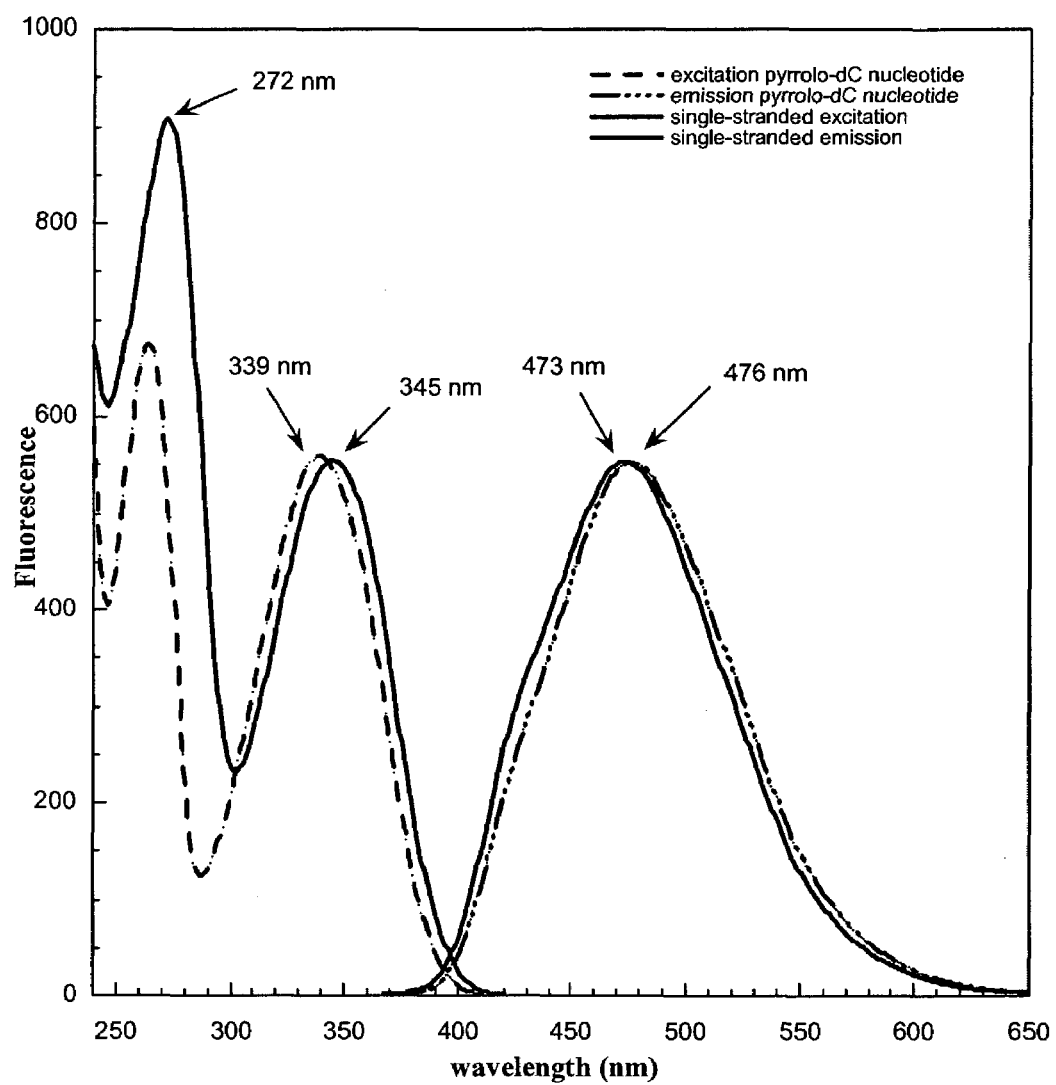
FIG. 1 shows excitation and emission spectra of pyrrolo-dC when in a single-stranded oligonucleotide having the sequence 5'-GCC TAA CTT CXG GAG ATG T-3' (SEQ ID NO.:1), where X is pyrrolo-dC, compared to the excitation and emission spectra of pyrrolo-dC 3'-phosphate.
Figure 2:
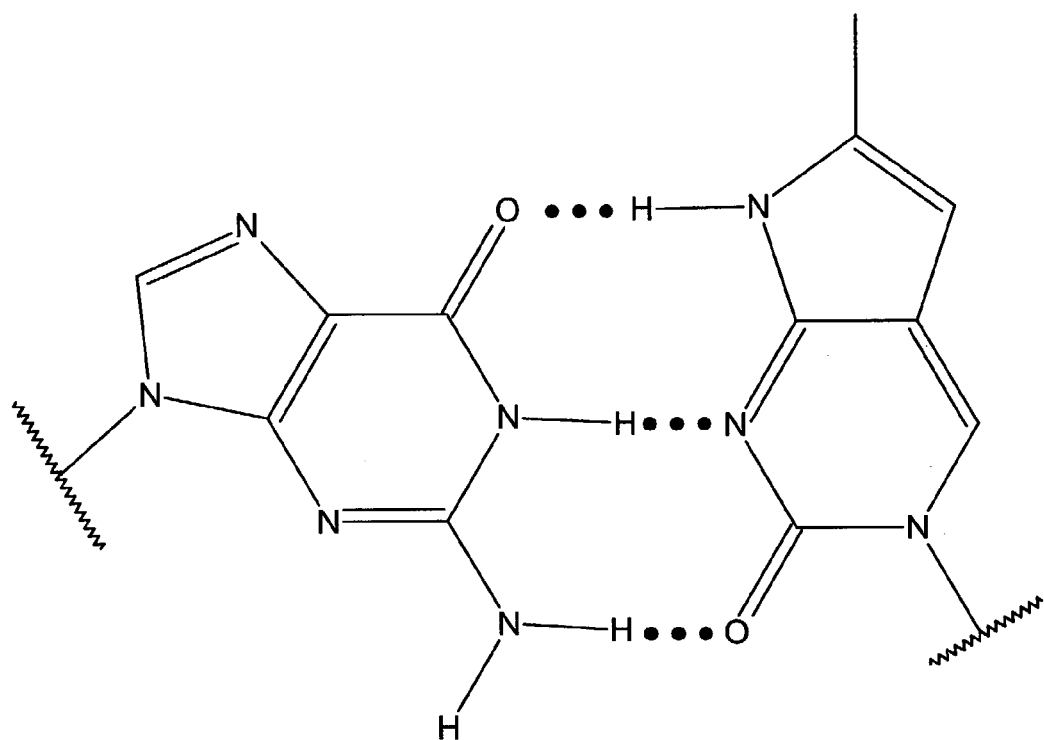
FIG. 2 is a base pairing model for guanine and pyrrolo-dC.
Figure 3:
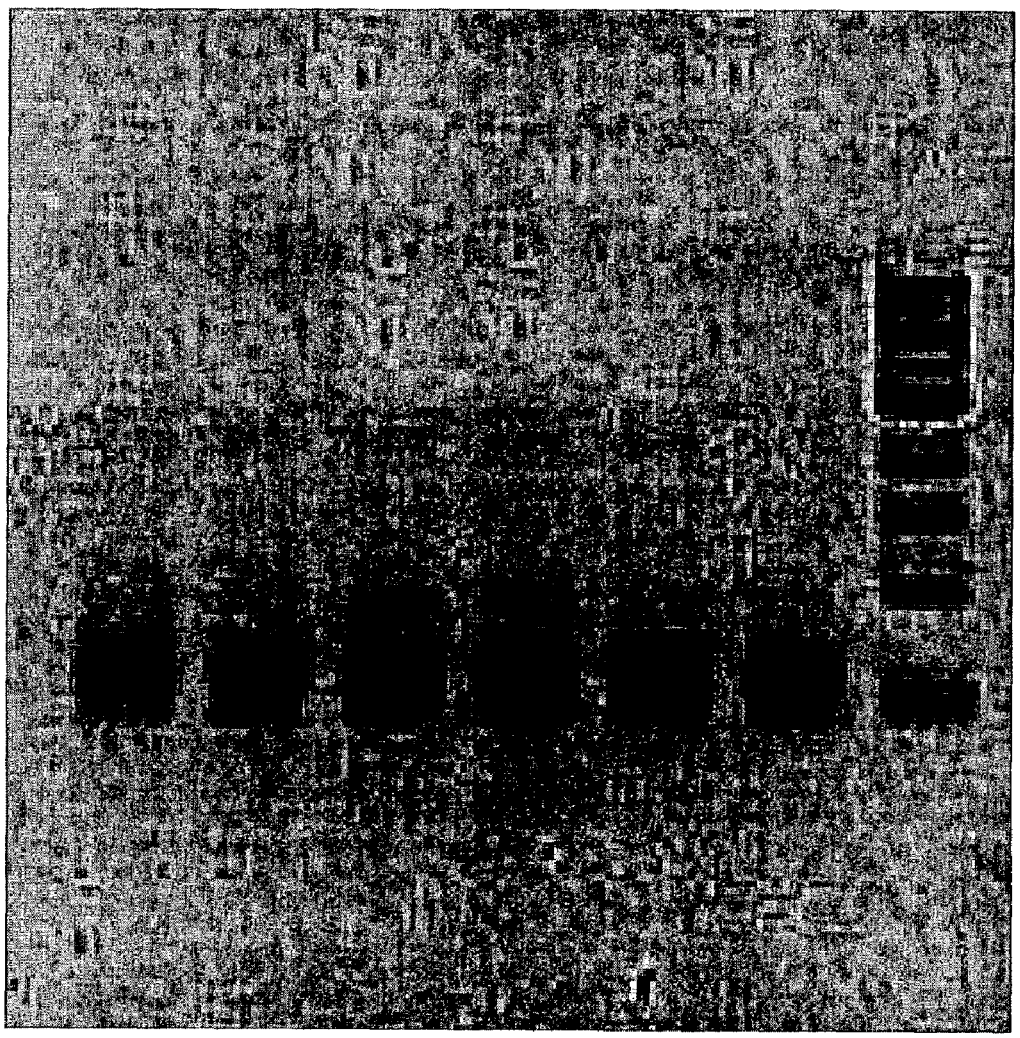
FIG. 3 is a gel showing the results of PCR amplification of a 600 nucleotide insert using pyrrolo-dC subsituted and unsubstituted primers (Sp6 and T7). Lanes 1 & 2 are control T7, Lanes 3–6 are T7 primer with 1 to 4 pyrrolo-dC substitutions and Lane 7 is oligo molecular weight marker (MWM) ladder.

The data and results shown in the figures will be recognized by those skilled in the art to represent exemplary data and results. Other data and results, consistent with this disclosure, can be readily obtained by those skilled in the art given the benefit of this disclosure.

DETAILED DESCRIPTION OF CERTAIN EXAMPLES

It will be recognized from the above description that the novel fluorescent nitrogenous bases disclosed here can be used in many applications. The precise use of the nitrogenous base and/or nucleosides incorporating the same will depend in large part on the particular application of the composition in which the nitrogenous base and/or nucleosides are incorporated. For convenience purposes only, in this detailed description of certain examples, the fluorescent nitrogenous base is generally used in conjunction with a sugar moiety to provide a nucleoside that can be used in nucleic acid synthesis, research, investigation, etc. It will be within the ability of those skilled in the art given the benefit of this disclosure, however, to use and to incorporate the fluorescent nitrogenous base in other compounds, suitable for these and other types of applications.

A. Compositions

In some examples, a composition of formula (I) is provided:

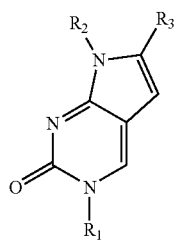

(I).

$R_1$ of formula (I) may be selected from the group consisting of hydrogen, a saturated or unsaturated hydrocarbon group, an aralkyl group, a cycloalkyl group, an aryl group, a heteroaryl group, or a saturated or partially saturated heterocyclic group, wherein these groups may be unsubstituted or substituted with one or more substituents, which are the same or different, selected from the group consisting of $R^7$, $OR^7$, $SR^7$, $NR^8COR^7$, $NR^8CSR^7$, $NR^8CO_2R^7$, $NR^8C(O)SR^7$, $NR^8CS_2R^7$, $O_2CR^7$, $S_2CR^7$, $SCOR^7$, $OCSR^7$, $SO_2R^7$, $OSO_2R^7$, $NR^8SO_2R^7$, $CN$, $NO_2$, $N_3$, and a halogen, wherein $R^7$ is an alkyl, an aryl or an aralkyl, each being unsubstituted or substituted with one or more halogen atoms, which are the same or different, and $R^8$ is hydrogen or an alkyl. Further, $R_1$ of formula (I) may be selected from the group consisting of a sugar moiety, a ribosyl group, a 2',2'-difluoro-2'-deoxyribosyl group, a 5'-(phosphoryloxy)ribosyl group, a 5'-(diphosphoryloxy)ribosyl group, a 5'-(triphosphoryloxy)ribosyl group, a 2'-deoxyribosyl group, a 5'-phosphoryloxy-2'-deoxyribosyl group, a 5'-diphosphoryloxy-2'-deoxyribosyl group, and a 5'-triphosphoryloxy-2'-deoxyribosyl group.

When a sugar moiety is present in compositions according to formula (I), the sugar moiety can be any saccharide, but preferably it is a saccharide selected from aldopentoses including ribose and 2'-deoxyribose. In some examples, the sugar moiety comprises a furanose form of an aldopentose, such as β-D-ribofuranosyl or β-D-2'-deoxyribofuranosyl. However, in certain embodiments, the sugar moiety may comprise any aldopentose, such as D-arabinosyl, D-xylosyl, D-2'-deoxyxylosyl, and D-lyxosyl. In yet other examples, the L enantiomer of a sugar moiety may be used, e.g., L-ribosyl, L-deoxyribosyl, etc. One skilled in the art, given the benefit of this disclosure, will be able to select suitable sugar moieties for incorporation into nucleosides comprising the composition of formula (I).

The sugar moiety may be linked to at least one phosphoryl group, e.g., through the 5' hydroxyl of the sugar moiety. In examples where the sugar moiety is linked to a single phosphoryl group and a composition in accordance with formula (I), the resulting nucleoside monophosphate may take a non-cyclized form or a cyclized form. For example, if the resulting nucleoside monophosphate is cyclized, preferably the phosphoryl group will be esterified to two of the available hydroxyl groups found in the sugar moiety, e.g., the 3' hydroxyl group of the sugar moiety and the hydroxyl group bound to the 5' carbon of the sugar moiety. Representative structures of 3',5'-cyclic nucleoside phosphates are shown in formulas (III)a and (III)b below:

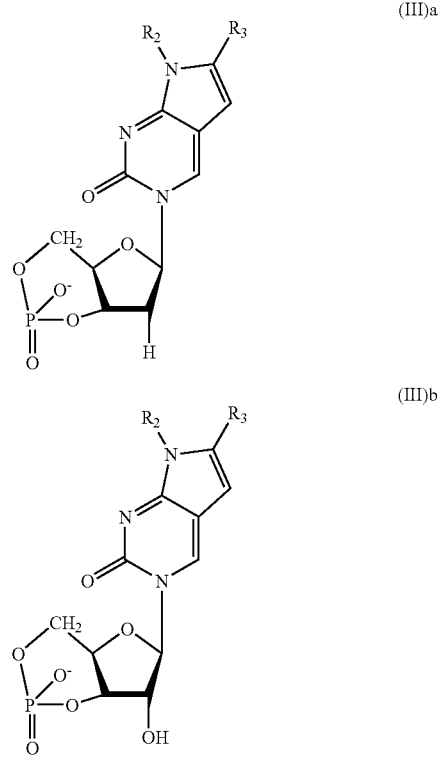

In each of compounds (III)a and (III)b, $R_2$ represents hydrogen, an acetyl group, or a group which is cleavable or hydrolyzable to yield a hydrogen or acetyl group and $R_3$ represents hydrogen or a saturated or unsaturated hydrocarbon having one to about eight carbons, more preferably about one to four or one to three and/or two to eight carbons, e.g., methyl, ethyl, propyl, cyclopropyl, propylene, isopropyl, butyl, cyclopropylmethyl, t-butyl and the like. Other cyclic forms may be possible and will be recognized by those skilled in the art given the benefit of this disclosure.

In some instances, the sugar moiety may be linked to the nitrogenous base through a β-glycosidic bond to N1 of the base. This β-glycosidic bond linkage is present in both non-cyclized and cyclized forms of nucleosides and nucleoside phosphates having the novel fluorescent base disclosed here.

Compounds according to formula (I), in at least some instances, may be capable of tautomerism, e.g., keto/enol tautomerism. For example, in compounds where $R_1$ represents hydrogen, as shown in formulas (I)a and (I)b below, the keto form (formula (I)a), which is also referred to as the lactam form, may be able to tautomerize to the enol form (formula (I)b), which is also referred to as the lactim or 2-hydroxypyrimidine form:

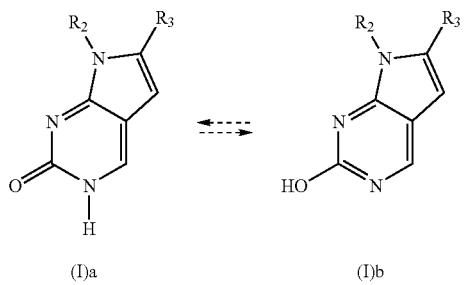

(I)a    (I)b

Other substituents may affect the form that is predominant under certain conditions. That is, the nature and properties of the other substituents, e.g., $R_2$ and $R_3$, may affect which form predominates under certain conditions. In addition, for reacting with other compounds, it might be desirable to favor one form over the other to achieve a desired product. One skilled in the art, given the benefit of this disclosure, will be able to select suitable conditions for favoring a selected form of compositions having formula (I). One skilled in the art will also recognize, given the benefit of this disclosure, that other tautomeric forms are possible. Without wishing to be bound by any particular scientific theory, such other tautomeric forms are believed to exhibit similar properties as the compositions disclosed here.

$R_2$ of formula (I) above may be selected from the group consisting of hydrogen or an acetyl group. Also, $R_3$ of formula (I) may be selected from the group consisting of hydrogen and a saturated or unsaturated hydrocarbon having one to four carbons or from about two to four carbons, e.g., methyl, ethyl, propyl, cyclopropyl, allyl, and isopropyl. Substituents $R_2$ and $R_3$ may be the same or different without departing from the scope of this disclosure. In certain examples, $R_3$ represents a saturated or unsaturated hydrocarbon such that no, or substantially minimal, hydrogen bonding occurs to the group attached to $R_3$. In certain examples, $R_1$ is hydrogen, $R_2$ is hydrogen, and $R_3$ is a methyl group. It will be recognized by those skilled in the art that the representative groups recited for $R_1$, $R_2$ and $R_3$ may be combined in any combination with each other, and the specific combinations disclosed here are only exemplary combinations.

Examples also relate to compositions according to formula (II) as shown below:

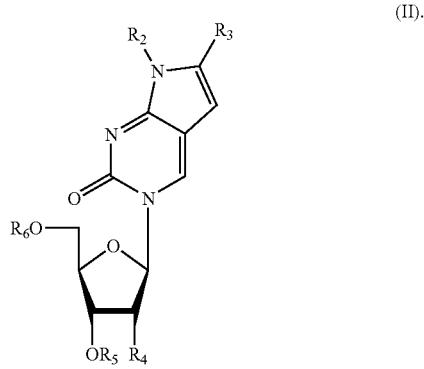

(II)

In formula (II), $R_2$ represents hydrogen or an acetyl group. $R_3$ represents hydrogen or saturated or unsaturated hydrocarbon having one to eight carbons, more preferably about one to three, two to about eight or one to about four carbons, e.g., methyl, ethyl, propyl, cyclopropyl, allyl, isopropyl, butyl, t-butyl and the like. $R_4$ represents hydrogen, a hydroxyl group, a protected hydroxyl group (e.g., t-butyldimethylsilyloxy or triisopropylsilyloxymethoxy), fluorine, an allyloxy group, an alkynylalkoxy group, an aminoalkoxy group, an aminoalkoxy group wherein the amino group bears a protecting group, or a methoxy group. $R_5$ represents hydrogen, an acetyl group, a phosphoryl group, a nucleoside phosphoryl group, a nucleoside thiophosphoryl group, an alkoxy-N,N-dialkylaminophosphinyl group (e.g., a 2-cyanoethoxy-N,N-diisopropylaminophosphinyl group or a methoxy-N,N-diisopropylaminophosphinyl group). $R_6$ represents hydrogen, a phosphoryl group, a diphosphoryl group, a triphosphoryl group, a nucleoside phosphoryl group, a nucleoside thiophosphoryl group, a polynuclotidyl group, and a protecting group removable under acidic, neutral, or photochemical conditions. Suitable protecting groups removable under acidic, neutral, or photochemical conditions include, but are not limited to, a dimethoxytrityl group, a monomethoxytrityl group, a pixyl group, a 2-(2-nitrophenyl)propoxycarbonyl (nppoc) group and the like. Other suitable protecting groups removable under acidic, neutral, or photochemical conditions will be readily recognized and selected by those skilled in the art given the benefit of this disclosure. In examples where $R_4$ represents a bis-(2-acetoxyethoxy)methoxy protecting group, $R_6$ may represent an alkoxybis(trimethylsilyloxy)silyloxy group, wherein the alkoxy group is cyclooctyloxy, cyclododecyloxy, or diphenylmethoxy. In yet other examples, the R groups of formula (II) are selected such that the resulting compounds 6-methyl-3-(β-D-2'-(substituted)-2'-deoxyribofuranosyl)pyrrolo[2,3-d]pyrimidin-2-one or 6-methyl-3-(β-D-2'-(substituted)-ribofuranosyl)pyrrolo[2,3-d]pyrimidin-2-one are provided.

The linkage of the sugar moiety to the pyrrolopyrimidine-C base in formula (II) may occur, in at least some examples, through a β-glycosidic bond to N1 of the heterocyclic base. This linkage can be present in both non-cyclized and cyclized forms of nucleosides having formula (II). In particular, in embodiments of formula (II) where $R_6$ represents a phosphate, the nucleoside may cyclize to form a cyclic nucleoside, as discussed above in conjunction with formulae (III)a and (III)b.

Also as discussed above, compounds having a composition in accordance with formula (II) may be able to form tautomers, e.g., keto/enol tautomers, under suitable conditions. The predominant tautomeric forms will typically depend on the nature and properties of the groups attached to the base. One skilled in the art given the benefit of this disclosure will be able to select conditions that favor a desired tautomeric form.

The nucleoside of formula (II) also may be linked to additional nucleosides through 5' and 3' phosphate linkages between nucleosides. In some examples, a nucleoside having formula (II) may be linked to two or more additional nucleosides, as shown below in formula (IV).

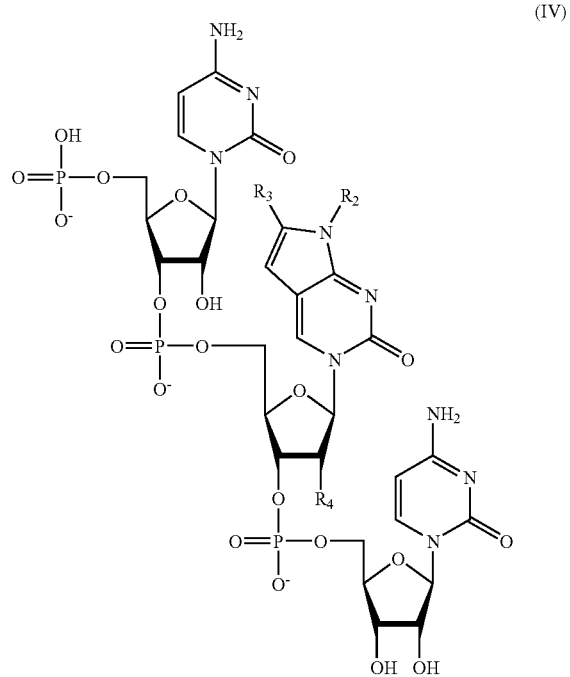

(IV)

If R$_4$ of formula (IV) represents a hydroxyl group, then formula (IV) represents three ribonucleosides linked through phosphodiester bonds, in which the sequence of the resultant ribonucleotides is 5'-CXC-3' (SEQ ID NO.:2), where C represents cytidine and X represents pyrrolo-C. Such ribonucleotides, or deoxyribonucleotides in the case where all the sugar moieties are 2'-deoxyribose, may be useful as a probe, for example, as further discussed below. In some examples, a plurality of pyrrolo-C or pyrrolo-dC molecules may be linked directly to each other, e.g., (X)$_n$ where X represents pyrrolo-C or pyrrolo-dC and n is greater than or equal to 1. Typically the number of linked pyrrolo-C or pyrrolo-dC bases is between 1 and 20, however the length is only limited by the practical limits of DNA or RNA synthesis, or other suitable synthetic routes, and, in certain examples, over 100, 1000, or more pyrrolo-C or pyrrolo-dC nucleosides may be linked directly together and/or linked to naturally occurring nucleosides. One skilled in the art given the benefit of this disclosure will be able to select and design suitable linked nucleosides for an intended use.

Compounds having formula (II) are generally shown above to include a hydrogen atom and R$_4$ attached to C2' and a hydrogen atom and OR$_5$ attached to C3'. In certain examples, however, one or more different groups can be substituted for hydrogen atoms attached to C2' and C3'. In certain examples, a halogen group is attached to C2' or C3' such that the nitrogenous base is attached to a sugar moiety having a halogen group and R$_4$ bonded to C2' and/or another halogen group and OR$_5$ bonded to C3'. Preferably the halogen group is fluorine. In certain examples two halogen groups are attached to the same carbon, e.g., R$_4$ is a fluoro group and C2' is attached to an additional fluoro group to form a 2',2'-difluoro compound. It will be within the ability of those skilled in the art given the benefit of this disclosure to design and use such other compounds.

In other examples, R$_3$ represents a saturated or unsaturated hydrocarbon such that no, or substantially minimal, hydrogen bonding occurs to the group attached to R$_3$. It will be recognized by those skilled in the art that the representative groups recited for R$_1$, R$_2$, R$_3$, R$_4$, R$_5$, and R$_6$ may be combined in any combination with each other, and the specific combinations disclosed here are only exemplary combinations. One skilled in the art given the benefit of this disclosure will be able to design and select specific compounds in accordance with formula (II) for an intended use.

B. Probes

In accordance with some examples, probes are provided. For example, a probe may be provided comprising at least one nucleoside in which the nitrogenous base of the at least one nucleoside is pyrrolopyrimidine-C, as shown in formula (I), or in which the nucleoside comprises a composition having formula (II). The probe may be operative to hybridize to a complementary oligonucleotide, since nucleosides having pyrrolopyrimidine-C as the nitrogenous base are capable of forming one or more hydrogen bonds with a nitrogenous base of another nucleoside, e.g., pyrrolopyrimidine-C can form three hydrogen bonds to guanine. Probes comprising a nucleoside in which pyrrolopyrimidine-C is the nitrogenous base may be flanked by one or more additional nucleosides. The additional nucleosides may include any of the naturally occurring nitrogenous bases and/or naturally occurring derivatives thereof, such as, for example, adenine, guanine, thymine, uracil, cytosine, hypoxanthine, xanthine, uric acid, and derivatives thereof (any of which may be present in either the keto or the enol forms if possible), or may include pyrrolopyrimidine-C. One skilled in the art, given the benefit of this disclosure, will be able to select and design suitable probes comprising nucleosides in which pyrrolopyrimidine-C may be the nitrogenous base.

A probe also may comprise a plurality of nucleosides directly linked to each other in which each of the nucleosides comprises a nitrogenous base having formula (I) or comprises a nucleoside having formula (II). The labeling of nucleotide sequences in synthetic oligonucleotides has been widely used in molecular biology as diagnostic probes for screening genomic and complementary DNA libraries, as primers for DNA synthesis, sequencing, and amplification, and in the study of DNA-protein interactions. See, for example, Landegren U., Kaiser, R., Caskey, C. T., Hood, L., Science, 1988, 242, 229–237. In certain more specific examples, a probe includes the nucleic acid sequence X$_1$X$_2$X$_3$ ... X$_n$, where X is any nitrogenous base including, but not limited to, adenine, guanine, thymine, uracil, cytosine, hypoxanthine, xanthine pyrrolo-C, pyrrolo-dC or pyrrolopyrimidine-C (or derivatives of any of them), and n is between about 1 and about 100, more typically between about 1 to about 50, and in some examples, about 1 to about 20 or even about 1 to about 5. Such probes can be synthesized, or expressed in a suitable host cell/vector construct, as discussed further below. Without wishing to be bound by any particular scientific theory, the fluorescence intensity of probes comprising pyrrolo-C and/or pyrrolo-dC is believed to increase with increasing numbers of pyrrolo-C and/or pyrrolo-dC. That is, as more pyrrolo-C and/or pyrrolo-dC nucleosides are included in the probe, the fluorescence intensity of the probe typically increases. Thus, depending on the required intensity necessary for detection of the probe, it may be possible to include a single pyrrolo-C or pyrrolo-dC nucleoside or a plurality of pyrrolo-C or pyrrolo-dC nucleosides in a given probe. One skilled in the art given the benefit of this disclosure will be able to select suitable numbers of pyrrolo-C and pyrrolo-dC nucleosides for incorporating into a probe depending on the intended use of the probe.

Probes in accordance with this disclosure have a variety of potential uses. For example, a probe in which pyrrolo-C or pyrrolo-dC has been substituted for cytidine may be useful in investigating metabolic function, disorders, and/or diseases. As an example, the enzyme telomerase is believed to add numerous repeats of the sequence TTAGGG (SEQ ID NO.:3), referred to below as the telomerase sequence, to eukaryotic chromosomes, such as those in humans and rodents. Thus, the complementary sequence AATCCC (SEQ ID NO.:4) can be constructed to hybridize to the telomerase sequence TTAGGG (SEQ ID NO.:3). However, due to the low fluorescence intensity of a probe having the sequence AATCCC (SEQ ID NO.:4), a probe having only the sequence AATCCC (SEQ ID NO.:4) provides limited utility for investigating telomerase sequences and the structure, e.g., secondary and tertiary structure, adopted by repeats of the telomerase sequence. In contrast, a probe comprising the sequence AATXXX (SEQ ID NO.:5), where X represents pyrrolo-C or pyrrolo-dC (as shown in formula (II), for example), may be useful in investigating the functions and/or structure of telomerase sequences. The sequence AATXXX (SEQ ID NO.:5) is complementary to the telomerase sequence, because pyrrolo-C, pyrrolo-dC and cytidine each hybridize similarly to guanine, e.g., each can form three hydrogen bonds to guanine. Thus, a probe comprising AATXXX (SEQ ID NO.:5) provides a fluorescent probe that can be used to investigate nucleic acid-nucleic acid interactions and provides information about the environment and properties of the hybridized nucleic acids. Additional probes can be designed to target sequences known to occur in other disorders, for example, $(GCG)_n$ repeats found in some muscular dystrophies and the guanine rich regions of the c-myc gene, one of the most commonly malfunctioning genes in human cancers. One skilled in the art given the benefit of this disclosure will be able to select suitable probe sequences for investigating a selected metabolic disorder or disease.

C. Isolated Polynucleotides

This disclosure also relates to various isolated polynucleotides. For example, one aspect of this disclosure relates to isolated polynucleotides comprising a plurality of nucleosides in which at least one nucleoside comprises a nitrogenous base in accordance with formula (I). In accordance with other examples, isolated polynucleotides comprising a plurality of nucleosides in which at least one nucleoside has a composition in accordance with formula (II) are provided. The isolated polynucleotides typically, though not necessarily, include between about 10 and about 1000 nucleotides, e.g., include between about 10 and about 100 nucleosides. The isolated polynucleotides may be either single stranded or double stranded and may comprise ribose, deoxyribose, mixtures thereof, or other suitable sugar moieties, as discussed above.

The polynucleotides can be synthesized using known chemical techniques, such as phosphoramidite chemistry. Using phosphoramidite chemistry, nucleosides can be sequentially added. Typically, such syntheses may be performed using solid-phase chemistry. Other suitable techniques for the chemical synthesis of polynucleotides will be readily selected by the person of ordinary skill in the art given the benefit of this disclosure.

In some examples, chemical synthesis of a polynucleotide occurs in the 3' to 5' direction. Typically, a nucleoside is bound to a solid support through the 3' hydroxyl group and has a blocking group (such as, for example, a dimethoxytrityl (DMT) group) to block reaction with the 5' hydroxyl group. In examples where the base of the bound nucleoside includes reactive $NH_2$ groups, then a suitable compound, such as benzoyl chloride or isobutyryl chloride, can be reacted with the base to produce a N-benzoyl or N-isobutyryl derivative, respectively, to prevent side reactions. The DMT group typically is removed from the bound nucleoside using an acid, such as trichloroacetic acid. A second nucleoside, in the form of a nucleoside phosphoramidite derivative, is then coupled to the bound nucleoside. Such step typically is catalyzed by a weak acid, such as tetrazole. Without wishing to be bound by any particular scientific theory, the weak acid is thought to activate the phosphoramidite so that rapid reaction between the free 5' hydroxyl group of the bound nucleoside and the phosphoramidite derivative occurs to form two nucleosides linked through a phosphite bond. Unreacted 5' hydroxyl groups of the bound nucleoside, e.g., those that did not react with the phosphoramidite derivative, can be capped with acetic anhydride to prevent any unwanted side products. The resulting phosphite-linked nucleosides can be oxidized to a phosphate group using suitable methods and reagents, such as, for example, treatment with an aqueous solution of iodine to oxidize the phosphite group to a phosphate group. Alternatively, oxidation with the Beaucage Reagent, 3H-1,2-benzodithiole-3-one-1,2-dioxide, 3-ethoxy-1,2,4-dithiazoline-5-one (EDITH) or tetraethylthiuram disulfide (TETD) will yield a phosphorothioate group. Oxidation with other reagents, such as borane-dimethylsulfide will yield boranophosphates. See, for example, REF Sood, A., Shaw, B. R., Spielvogel, B. F., *J. Am. Chem. Soc.*, 112, 9000–9001, (1990). Other suitable methods and reagents for oxidation of the phosphite group will be readily selected by those skilled in the art, given the benefit of this disclosure. The result is two linked nucleosides in which the added nucleoside includes a dimethoxytrityl group bonded to the 5' hydroxyl group of the added nucleoside. This process can be repeated until the desired number of nucleosides are added to the nucleoside chain.

When it is desirable to cleave the linked nucleosides from the solid phase support, a solution of base, such as ammonium hydroxide ($NH_4OH$) can be added. The ammonium hydroxide can also remove any N-benzoyl or N-isobutyryl groups that were added during synthesis. One skilled in the art, given the benefit of this disclosure, will be able to chemically synthesize selected polynucleotides in accordance with these and other methods. For example, genes such as tRNA (126 bp), $H_{174}$, a member of the CXC Chemokine family (453 bp), α/β-interferon receptor (896 bp), and tissue plasminogen activator (1610 bp) can be synthesized using nucleosides including the novel fluorescent nitrogenous base disclosed here and chemical synthetic techniques known to those skilled in the art. In some examples, the polynucleotide includes between about 2 and about 2000 base pairs, preferably between about 10 and about 1000 base pairs, in some examples between about 15 and 500 base pairs, including, for example, 18–25, 30, 35, 40, 45 and/or 50 base pairs. One skilled in the art given the benefit of this disclosure will be able to synthesize polynucleotides having a selected number of base pairs.

D. Vectors

An isolated polynucleotide also may be amplified by insertion of a suitable nucleic acid sequence into a suitable host cell, e.g., using vectors and the like. The inserted nucleic acid will be replicated along with any host cell nucleic acid. The nucleic acid can be isolated from the host cells using standard chemical techniques, such as centrifugation, chromatography, electrophoresis, and the like. One skilled in the art given the benefit of this disclosure will be able to amplify and isolate polynucleotides using vector and host cells systems, some of which are described in detail below.

As one example, a vector comprising at least one nucleoside in which the nitrogenous base of the at least one nucleotide has a composition in accordance with formula (I) is provided. As used here, "vector" refers to a vehicle, such as a single-stranded or double-stranded nucleic acid molecule, that can transport nucleic acid molecules, e.g., that can transport nucleic acid molecules into a host cell. As another example, a vector comprising at least one nucleoside in accordance with formula (II) is provided. In some instances, the vector comprises a gene that has been inserted into the vector. The gene preferably includes at least one nucleoside in which the nitrogenous base of the at least one nucleoside has a composition in accordance with formula (I) or at least one nucleoside in accordance with formula (II). Generally, any system or vector suitable to maintain, propagate or express polynucleotides in a host may be used. For example, any vector that is operative to receive a nucleic acid sequence comprising cytidine should also be operative to receive a nucleic acid sequence comprising at least one nucleoside in which the nitrogenous base of the at least one nucleoside has a composition in accordance with formula (I) or includes at least one nucleoside in accordance with formula (II). In certain examples, a vector can be maintained in the host cell as an extrachromosomal element where it replicates and produces additional copies of the nucleic acid molecules. In other examples, a vector may integrate into the host cell genome and produce additional copies of the nucleic acid molecules when the host cell replicates. The gene can be inserted into the vector using well-known methodologies. Generally, the nucleic acid sequence that will ultimately be expressed is joined to an expression vector by cleaving the nucleic acid sequence and the expression vector with one or more restriction enzymes, such as endonucleases or exonucleases, and then ligating the fragments together, using a suitable ligase or polymerase, for example. Procedures for restriction enzyme digestion and ligation will be readily selected by those skilled in the art.

Exemplary vectors include, but are not limited to: chromosomal-, episomal- and virus-derived vectors, for example, vectors derived from bacterial plasmids, from bacteriophages, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses, picornaviruses and retroviruses, and vectors derived from combinations thereof, such as those derived from plasmid and bacteriophage genetic elements, such as cosmids and phagemids, artificial chromosomes, such as BAC, PAC, YAC, or MAC, and other vectors commercially available from such manufacturers as Invitrogen Corp. (Carlsbad, Calif.), Nature Technology Corp. (Lincoln, Nebr.) and Ambion, Inc. (Austin, Tex.), for example. Other suitable cloning vectors for prokaryotic and eukaryotic hosts are described in Sambrook et al., *Molecular Cloning: A Laboratory Manual.* 2nd. ed., Cold Spring Harbor Laboratory Press, Cold Spring Harbor, N.Y., (1989). One skilled in the art, given the benefit of this disclosure, will be able to select these and other suitable vectors depending on an intended use.

In other examples, vectors may further include one or more reporters. Potential reporter genes include, but are not limited to: β-galactosidase, β-lactamase, bacterial luciferase, firefly luciferase, β-glucuronidase. Without wishing to be bound by any particular scientific theory, it is believed that the reporter genes can be used to evaluate whether or not a gene has been inserted into a vector. One skilled in the art given the benefit of this disclosure will be able to select and incorporate these and other reporters into suitable vectors.

In accordance with yet other examples, the vector may further include one or more promoters. Preferably, the promoter is cloned upstream of the gene such that activation of the promoter will result in transcription of the gene. In some instances, the promoter is inducible such that addition of a compound or substance results in replication, transcription and/or translation. Thus, the promoters can be used to drive the synthesis of genes that have been inserted into the vector. Preferably, the promoter is a promoter that is inducible by lactose, mannose or by other suitable inducers. Exemplary promoters include, but are not limited to, the left promoter from bacteriophage λ, the lac, TRP, and TAC promoters from *E. coli*, the early and late promoters from SV40, the CMV immediate early promoter, the adenovirus early and late promoters, retrovirus long-terminal repeats, and the like. Other suitable promoters will be readily selected by those skilled in the art given the benefit of this disclosure.

In addition to containing sites for transcription initiation and control, vectors also may contain sequences necessary for transcription termination and, in the transcribed region, a ribosome-binding site for translation. Other regulatory control elements for expression include initiation and termination codons as well as polyadenylation signals, for example. One skilled in the art given the benefit of this disclosure will be able to select and incorporate suitable regulatory sequences that are useful in vectors. Exemplary regulatory sequences are described, for example, in Sambrook et al., *Molecular Cloning: A Laboratory Manual.* 2nd. ed., Cold Spring Harbor Laboratory Press, Cold Spring Harbor, N.Y., (1989).

A host cell may include a vector according to this disclosure, as described above. The vector containing the appropriate nucleic acid molecule can be introduced into an appropriate host cell for propagation or expression using well-known techniques. Suitable host cells include, but are not limited to: bacterial cells, such as *E. coli, Streptomyces*, and *Salmonella typhimurium*; eukaryotic cells, such as yeast cells; insect cells, such as *Drosophila*; mammalian cells, such as COS and CHO cells; and plant cells. Other host cells may be readily selected by those skilled in the art given the benefit of this disclosure, and additional exemplary host cells are described in Sambrook et al. described above.

In other examples, a chimeric or fusion protein can be produced by standard recombinant DNA techniques. For example, DNA fragments, some of which may include pyrrolo-dC, coding for the different protein sequences are ligated together in-frame in accordance with conventional techniques. In other examples, the fusion gene can be synthesized by conventional techniques including chemical synthesis and/or automated DNA synthesizers. Alternatively, PCR amplification of gene fragments can be carried out using anchor primers, which give rise to complementary overhangs between two consecutive gene fragments that can subsequently be annealed and re-amplified to generate a chimeric gene sequence (see, for example, Ausubel et al., Current Protocols in Molecular Biology, 1992). Moreover, many expression vectors are commercially available that already encode a fusion moiety (e.g., a GST protein or a HIS tag protein). A transporter peptide-encoding nucleic acid can be cloned into such an expression vector such that the fusion moiety is linked in-frame to the transporter peptide. Such expression systems provide for rapid isolation and identification of expressed proteins. One skilled in the art, given the benefit of this disclosure, will be able to select suitable protein expression systems.

E. Kits

The present disclosure also relates to kits for producing a polynucleotide comprising free nucleotides and at least one enzyme, such as, for example, a polymerase. The free nucleotides include at least one nucleotide that includes a nitrogenous base in accordance with formula (I) or a nucleoside in accordance with formula (II). The polymerase may be any polymerase that is operative to join free nucleotides together. Preferably, the polymerase is selected from Taq DNA Polymerase, Pfu DNA polymerase, Vent DNA polymerase or an RNA polymerase such as T7 RNA polymerase. In examples where it is desirable to substitute pyrrolo-dC or pyrrolo-C for every possible occurrence of cytidine, the kit may include dATP, dGTP, dTTP and pyrrolo-dCTP or pyrrolo-CTP as the free nucleotides. Thus, when a DNA template is amplified, pyrrolo-dCTP will hybridize to guanine and the polymerase will join the pyrrolo-dCTP to adjacent dNTPs. One skilled in the art, given the benefit of this disclosure, will be able to select these and other suitable components for including in the kit to produce a polynucleotide.

F. Fluorescent Markers

In accordance with certain examples, a fluorescent marker having a composition in accordance with formula (I) or formula (II) is provided. Fluorescent labeled nucleotides have been employed in DNA sequencing. See, for example, Prober et. al., *Science*, 1987, 238:336–341. Presently, oligonucleotides are fluorescently labeled in two manners. In one case, the oligonucleotide is labeled with a fluorescent marker, or a fluorophore such as fluorescein, either through a carbon chain linkage at the 3'- or 5'-terminus or by covalent connection to a nucleobase in the oligonucleotide. These types of markers have the disadvantage of being relatively large and generally alter the interaction of the tagged oligonucleotide with other oligonucleotides or molecules through either steric hindrance or undesired interactions.

In the second case, oligonucleotides are modified to contain a nucleobase that is in itself fluorescent. A few examples reported for this type of fluorescent label include: ethenoadenosine, (Barrio, J. R., Secrist III, J. A., and Leonard, N. J., *Biochem. Biophys. Res. Commun.* 1972, 46, 597); ethenocytidine (ibid.); and a limited number of pteridine nucleosides including 3-methylisoxanthopterin-2'deoxyribofuranoside (Hawkins, M. E., Pfleiderer, W., Mazumder, A., Pommier, G., and Balis, F. M., Nucleic Acids Research, 1995, 23, 2872–2880). While these examples have been reported, they have been found to be of limited use due to their inability, because of their structural make-up, to bind to oligonucleotides of complementary sequences through hydrogen bonding and base-pairing to form Watson-Crick base-pair duplexes with cellular nucleic acids. 2-Aminopurine is a mildly fluorescent base, which has found significant use in probing DNA structures (see, for example, Jean, J. M. and Hall, K. B., *Proc. Natl. Acad. Sci. U.S.A.*, 2001, 98, 37–41).

In contrast, in certain examples disclosed here, nucleosides including the nitrogenous base disclosed here provide for fluorescent markers that are operative to hybridize to guanine using, for example, hydrogen bonding. Thus, the novel fluorescent nitrogenous base disclosed here provides for an intrinsic fluorescent marker. Such advantageous and unexpected properties allow for investigating of nucleic acid and protein structure without the disruptions and problems commonly observed with extrinsic fluorescent markers.

G. Preparation Methods

Methods of producing the target compositions having formula (I) or formula (II) also are provided as part of the present disclosure. General synthetic chemistry methods to prepare some of the compounds will be readily apparent to those skilled in the art given the benefit of this disclosure. The chemistry typically involves the initial conventional synthesis of the desired 5-alkynyluridines (V) prepared by palladium-catalyzed coupling of terminal alkynes with an appropriate 5-iodonucleoside using, for example, the methods described by Robins, et al., *J. Org. Chem.*, 1983, 48, 1854–1862]. Compounds of the type 3-(2-deoxy-β-D-ribofuranosyl)-2,3-dihydrofuro[2,3-d]pyrimidin-2-one (VI, where $R_3$=alkyl groups of six carbons or greater in length) have been reported by treatment of the corresponding compounds (V) with copper iodide in boiling methanol; McGuigan, C., et al., *J. Med. Chem.* 1999, 42, 4479–4484. These nucleosides were also converted to the corresponding 3-(2'-deoxy-β-D-ribofuranosyl)pyrrolo[2,3-d]pyrimidin-2-one (VII, where $R_3$=alkyl groups of six carbons or greater in length) by treatment of the above 3-(2-deoxy-β-D-ribofuranosyl)-2,3-dihydrofuro[2,3-d]pyrimidin-2-ones (VI, where $R_3$=alkyl groups of six carbons or greater in length) with ammonia or alkylamine. See McGuigan, C., et al., *Antiviral Chem. and Chemotherapy*, 2000, 11, 343–348. In addition to these preparations, Inoue et. al., Jpn Kokai JP 62059293, (1987) and in *Nippon Kagaku Kaishi*, 7, 1214–1220, 1987, reported on the preparation of 3-(2-Deoxy-β-D-ribofuranosyl)-pyrrolo[2,3-d]pyrimidin-2-one (VII, where $R_3$=H, and the n-butyl derivative), and their incorporation into DNA segments. Another oligodeoxynucleotide containing, 3-(2'-Deoxy-β-D-ribofuranosyl)pyrrolo[2,3-d]pyrimidin-2-one (VII, where $R_3$=H) by has been reported. This oligodeoxynucleotide was prepared by a post synthetic procedure. In this case, a oligodeoxynucleotide containing 3-(2-deoxy-β-D-ribofuranosyl)-2,3-dihydrofuro[2,3-d]pyrimidin-2-one was prepared, and, subsequently treated with ammonia, to convert, in situ, this oligodeoxynucleotide to one containing 3-(2'-Deoxy-β-D-ribofuranosyl)pyrrolo[2,3-d]pyrimidin-2-one (VII, where $R_3$=H). See Gamper and coworkers in *Nucleic Acids Research*, 24, 2470–2475, 1996.

Methods of producing compositions having formula (I) or formula (II) also are provided. The methods typically include adding a compound having formula (V) to a suitable solvent. Suitable solvents include but are not limited to methanol, acetone, ethanol, tetrahydrofuran, dichloromethane, and the like. To this mixture an amine, such as diethylamine or triethylamine, and a copper halide, e.g., CuCl, CuBr, CuI, is added. The mixture is refluxed until sufficient starting material has reacted. Formula (V) is provided below.

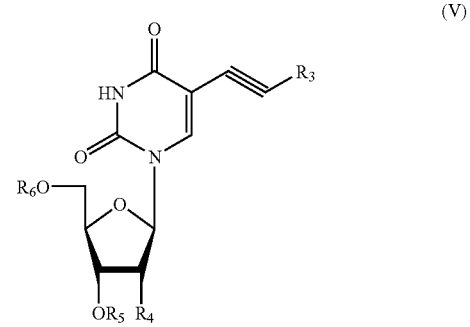

(V)

In formula (V), $R_3$ is hydrogen or a saturated or unsaturated hydrocarbon having one to eight carbons, e.g., methyl, ethyl, ethylene, propyl, allyl, isopropyl, butyl. $R_4$ represents hydrogen, a hydroxyl group, a protected hydroxyl group (e.g., a tert-butyldimethylsilyloxy group, a triisopropylsilyloxymethoxy group, or a 1-(2-fluorophenyl)-4-methoxypiperidin-4-yloxy group), fluorine, an allyloxy group, an alkynylalkoxy group, an aminoalkoxy group, an aminoalkoxy group wherein the amino group bears a protecting group, and a methoxy group. $R_5$ represents hydrogen, an acetyl group, a phosphoryl group, a nucleoside phosphoryl group, and a polynuclotidyl group. $R_6$ represents hydrogen, a phosphoryl group, a diphosphoryl (pyrophosphoryl) group, a triphosphoryl group, a dimethoxytrityl group, a nucleoside phosphoryl group, a polynuclotidyl group, or a protecting group removable under acidic, neutral, or photochemical conditions.

The product (VI) may be isolated in numerous ways. A first method for isolating the product involves concentrating the product in vacuo, and the remaining residue is partitioned between an organic phase (typically ether, ethyl acetate, or methylene chloride) and an aqueous solution of a chelating agent in a weak base, such as EDTA in a sodium bicarbonate solution. The organic phase is then dried using a drying agent, such as sodium sulfate, magnesium sulfate, or calcium sulfate. The dried organic phase is filtered and concentrated in vacuo to yield a crude product having formula (VI). The product is then recrystallized or purified, e.g., using suitable chromatographic methods, such as column chromatography. A second method for isolating the product involves adsorption onto suitable media, such as a selective adsorbent like Florisil® (a synthetic magnesia—silica gel available from Mallinckrodt Chemicals) and column purification using the selective adsorbent as the stationary phase, for example. The adsorbed compounds are eluted with organic solvent pairs, such as methylene chloride/methanol, to yield compounds that have a composition in accordance with formula (VI). Formula (VI) is shown below:

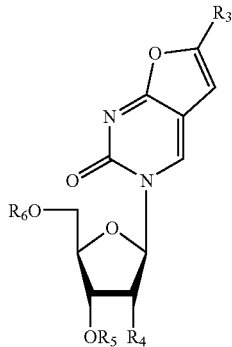

(VI).

In formula (VI), $R_3$ is hydrogen or a saturated or unsaturated hydrocarbon having one to eight carbons, e.g., methyl, ethyl, propyl, allyl, isopropyl, butyl, t-butyl and the like. $R_4$ represents hydrogen, a hydroxyl group, a protected hydroxyl group (e.g., a tert-butyldimethylsilyloxy group, a triisopropylsilyloxymethoxy group, or a 1-(2-fluorophenyl)-4-methoxypiperidin-4-yloxy group), fluorine, an allyloxy group, an alkynylalkoxy group, an aminoalkoxy group, an aminoalkoxy group wherein the amino group bears a protecting group, and a methoxy group. $R_5$ represents hydrogen, an acetyl group, a phosphoryl group, a nucleoside phosphoryl group, and a polynuclotidyl group. $R_6$ represents hydrogen, a phosphoryl group, a diphosphoryl (pyrophosphoryl) group, a triphosphoryl group, a dimethoxytrityl group, a nucleoside phosphoryl group, a polynuclotidyl group, or a protecting group removable under acidic, neutral, or photochemical conditions.

Compounds in accordance with formula (VI) may be dissolved in a solution of ammonia, e.g., 7 M $NH_3$ in methanol, and placed in a suitable vessel (such as a pressure vessel) for heating at a suitable temperature, e.g., about 50–60° C., for about 1–3 days or until substantially all the starting material has reacted. Suitable reactants other than ammonia in methanol also may be used without departing from this disclosure. The vessel is then cooled to about 5° C. in an ice bath and opened. The extent of the reaction may be monitored using chromatography, such as thin layer chromatography. Without wishing to be bound by any particular scientific theory, it is believed that the desired product runs slower than that of the starting material using 10:1 dichloromethane:methanol as the mobile phase. Once the reaction was complete, the reaction mixture may be concentrated in vacuo to yield a crude product. The crude products may be purified in any suitable manner, such as by recrystallization or chromatography, to afford compounds in accordance with formula (VII):

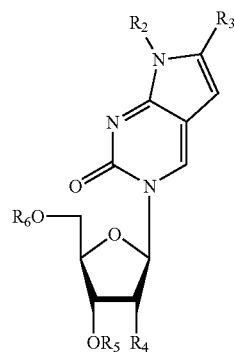

(VII).

In formula (VII), $R_2$ represents hydrogen. $R_3$ represents a saturated or unsaturated hydrocarbon having one to eight carbons, e.g., methyl, ethyl, propyl, allyl, and isopropyl. $R_4$ represents hydrogen, a hydroxyl group, a protected hydroxyl group (e.g., a tert-butyldimethylsilyloxy group, a triisopropylsilyloxymethoxy group, or a 1-(2-fluorophenyl)-4-methoxypiperidin-4-yloxy group), fluorine, an allyloxy group, an alkynylalkoxy group, an aminoalkoxy group, an aminoalkoxy group wherein the amino group bears a protecting group, and a methoxy group. $R_5$ represents hydrogen, an acetyl group, a phosphoryl group, a nucleoside phosphoryl group, and a polynuclotidyl group. $R_6$ represents hydrogen, a phosphoryl group, a diphosphoryl (pyrophosphoryl) group, a triphosphoryl group, a dimethoxytrityl group, a nucleoside phosphoryl group, a polynuclotidyl group, or a protecting group removable under acidic, neutral, or photochemical conditions.

In some examples, compounds in accordance with formula (VII) may be incorporated into DNA or RNA, for example, using suitable nucleic acid synthesizers. To do so, in at least some examples, 3'-O-phosphoramidites, either as the O-methyl or O-(2-cyanoethyl) forms may be used. An example procedure follows. Compounds in accordance with formula (VII) are first protected as their 5'-O-dimethoxytrityl derivatives according to standard literature protocols, then dissolved in a suitable amount of a suitable solvent, e.g., 30–50 mL of anhydrous dichloromethane. To this solution, a suitable phosphitylating agent is added, such as 2-cyanoethyl tetraisopropylphosphorodiamidite or methyl tetraisopropylphosphorodiamidite, 0.1 to 1 equivalents of a weak acid, such as tetrazole, may be necessary to carry out the reaction depending on the selected phosphitylating agent. The reaction is stirred at room temperature for about 4–8 hours or until substantially all of the starting material has reacted. The extent of the reaction may be monitored using chromatography, such as thin layer chromatography.

Once the reaction is substantially complete, the reaction mixture is washed with a weak base, such as 5% aqueous sodium bicarbonate, and the organic layer is dried over a suitable drying agent, such as sodium sulfate, magnesium sulfate, calcium sulfate, and the like. The reaction mixture may be cooled, if necessary, e.g., in an ice bath, prior to washing it with the weak base. After the drying agent is removed, the organic layer is concentrated in vacuo to afford a resinous product. Chromatography is used to purify the organic solvent mixtures using a suitable mobile phase, such as dichloromethane/methanol/triethylamine or ethyl acetate/hexane/triethylamine. The resulting compounds have a structure in accordance with formula (VIII), where DMT represent dimethoxytrityl:

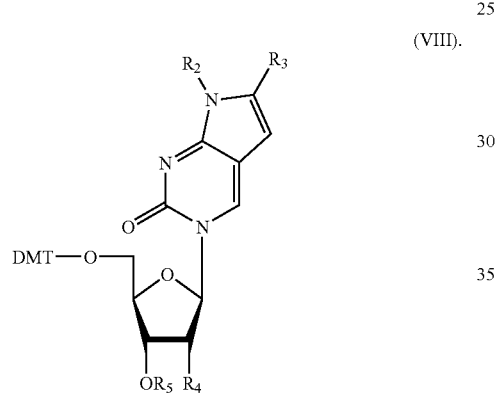

(VIII).

In this formula, $R_2$ represents hydrogen or an acetyl group; $R_3$ represents a saturated or unsaturated hydrocarbon having one to eight carbons, e.g., methyl, ethyl, propyl, allyl, and isopropyl. $R_4$ represents hydrogen, a hydroxyl group, a protected hydroxyl group (e.g., a tert-butyldimethylsilyloxy group, a triisopropylsilyloxymethoxy group, or a 1-(2-fluorophenyl)-4-methoxypiperidin-4-yloxy group), fluorine, an allyloxy group, an alkynylalkoxy group, an aminoalkoxy group, an aminoalkoxy group wherein the amino group bears a protecting group, and a methoxy group. $R_5$ represents an alkoxy-N,N-dialkyaminophosphinyl group (e.g., a 2-cyanoethoxy-N,N-diisopropylaminophosphinyl group or a methoxy-N,N-diisopropylaminophosphinyl group).

At least some phosphoramidites in accordance with formula (VIII) may be readily incorporated into oligonucleotides using standard phosphoramidite chemistry without requiring any modification of the coupling time of the DNA synthesis cycle. Oxidation and deprotection may be accomplished using numerous methods, for example, using an aqueous solution of $I_2$ (e.g., 0.01–0.1 M) for oxidation and an aqueous ammonium hydroxide solution (e.g., 15–40%) for deprotection. Alternatively, oxidation with the Beaucage Reagent, 3H-1,2-benzodithiole-3-one-1,2-dioxide, 3-ethoxy-1,2,4-dithiazoline-5-one (EDITH) or tetraethylthiuram disulfide (TETD) will yield a phosphorothioate group. Oxidation with other reagents, such as borane-dimethylsulfide will yield boranophosphates. See, for example, R E F Sood, A., Shaw, B. R., Spielvogel, B. F., *J. Am. Chem. Soc.*, 112, 9000–9001, (1990). At least some compounds in accordance with formula (VIII) have been shown to be compatible with Beaucage Sulfurizing Reagent, which allows for the synthesis of phosphorothioate oligos.

If desired, one or more phosphates may be added to compounds in accordance with formula (VIII). The phosphate and triphosphate forms can be prepared using routine methods known to those skilled in the art, for example those methods discussed in: J. Ludwig, Proceedings of the 2nd International Symposium on Phosphorus Chemistry Directed Towards Biology, 1987, 201–204, published by Elsevier Science Publishers B.V., Amsterdam. The resulting compounds generally have a composition in accordance with formula (IX)a–c:

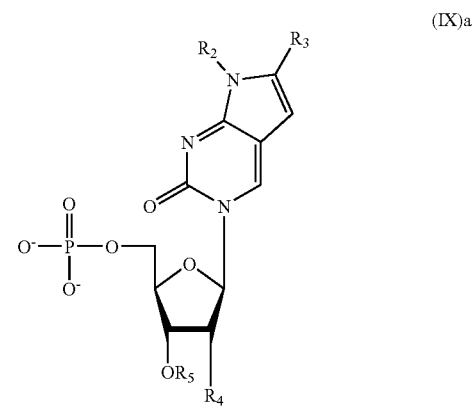

(IX)a

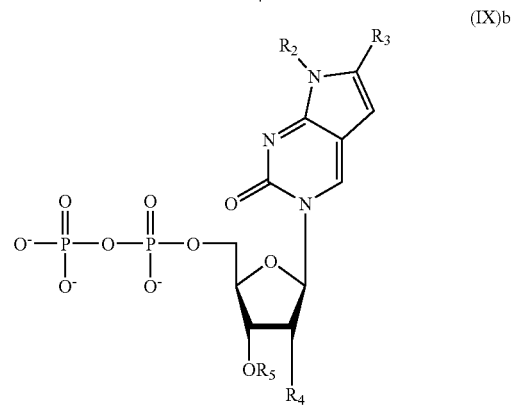

(IX)b

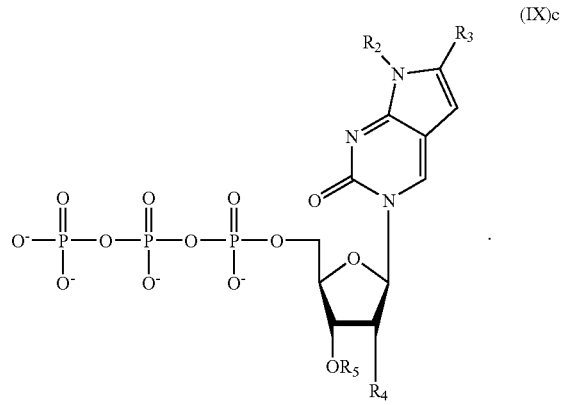

(IX)c

In compositions having formula (IX)a–c, $R_2$ represents hydrogen or an acetyl group; $R_3$ represents hydrogen or a saturated or unsaturated hydrocarbon having one to eight carbons, e.g., methyl, ethyl, propyl, allyl, and isopropyl; $R_4$ represents hydrogen, a hydroxyl group, a protected hydroxyl group (e.g., a tert-butyldimethylsilyloxy group, a triisopropylsilyloxymethoxy group, or a 1-(2-fluorophenyl)-4-methoxypiperidin-4-yloxy group), fluorine, an allyloxy group, an alkynylalkoxy group, an aminoalkoxy group, an aminoalkoxy group wherein the amino group bears a protecting group, and a methoxy group; and $R_5$ represents hydrogen or an acetyl group. In compositions of formula (IX)a–c, the phosphoryl groups may be protonated or deprotonated, depending on the pH of the solution.

The present disclosure also relates to methods of producing a probe or a polynucleotide including at least one nucleoside in which the at least one nucleoside comprises a nitrogenous base having the composition of formula (I) or a nucleoside in accordance with formula (II). The method includes selecting a desired nucleic acid sequence and chemically synthesizing the selected nucleic acid sequence using the methods described here and other methods well known to those skilled in the art. The nucleic acid sequence can be amplified using polymerase chain reaction methods or can be amplified in a vector/host cell system as discussed above, for example. Isolation and purification of the probe can be accomplished using standard analytical techniques including, but not limited to, chromatography (such as column chromatography, LC, FPLC, HPLC and the like), centrifugation, electrophoresis (such as polyacrylamide and agarose electrophoresis) and the like. Other suitable methods for isolating and purifying probes will be readily selected by those skilled in the art given the benefit of this disclosure.

Nucleosides in accordance with formula (II) can be added in a suitable form, e.g., a salt form such as a chloride salt, to media in which bacteria, yeast, insect cells, or other host cells are growing. Without wishing to be bound by any particular scientific theory, it is believed that growing cells may be able to uptake nucleosides having compositions in accordance with formula (II). After uptake of the nucleosides by the cells, the cells can use the nucleosides during replication of the host cell nucleic acids. Thus, nucleosides having a composition in accordance with formula (II) will be incorporated into the chromosomal and/or extrachromosomal nucleic acids in the host cells. One skilled in the art, given the benefit of this disclosure, will be able to select suitable forms and suitable amounts for incorporating compositions having formula (II) into media for growing host cells.

In some examples compounds in accordance with formula (II) can be treated under suitable conditions such that cleavage of the N-glycosidic bond between the nitrogenous base and the sugar moiety occurs releasing free nitrogenous base having a composition in accordance with formula (I). This reaction may be catalyzed by an catalyst or enzyme, such as, for example, a deaminase, a nucleotidase, a nucleoside phosphorylase, a N-glycosylase, ricin, α-tricosanthin ribosome inactivating proteins, saporins, amarandins and the like. In other examples, treatment of the compounds having formula (II) with one or more cleaving agents, such as, for example, hydrazine or aqueous acid, can yield free nitrogenous bases having formula (I). The free nitrogenous base can be isolated using standard analytical techniques, such as, for example, chromatography, centrifugation, electrophoresis, and the like. One skilled in the art given the benefit of this disclosure will be able to H. Example Uses Methods of administering a therapeutic amount of a composition including formula (I) or formula (II) also are provided. In some examples, a therapeutic amount, or an efficacious amount as the case may be, of a composition having formula (II) is administered to a mammal, such as a human.

Administration of cytidine and uridine has been reported to be effective in enhancing the regeneration of the liver in rats acutely poisoned with carbon tetrachloride. See, for example, Bushma, M. I., et al., *Bull. Exp. Biol. Med.* 88:1480–1483 (1980). Administration of cytidine and uridine has also been reported to be effective in the treatment of various neurological and myological conditions in animals, such as treatment for convulsions, cerebrovascular disorders, circulation disorders and the like. Without wishing to be bound by any particular scientific theory, because the novel fluorescent nitrogenous base disclosed here functions similarly to cytosine, administration of a composition including formula (II) is expected to provide similar metabolic and therapeutic actions as cytidine. Thus, compositions having formula (II) may be administered, either alone or with additional compounds such as uridine, to treat various disorders and in particular those disorders that responds favorably by administration of cytidine, cytosine, and/or derivatives thereof, e.g., acute myelocytic leukemia, diseases associated with DNA methylation, lung cancer, ovarian cancer, etc. See for example, Lund et al., *J. Natl. Cancer Inst.*, 1994, 86-1530–1533; Chabner, *Cancer Chemotherapy: Principles and Practice*, 2nd Ed., 1995, J. B. Lippincott Co. Preferably, compositions having formula (I) or formula (II) are administered as antineoplastic agents to an individual in need of treatment.

While it is possible to administer compounds having formula (I) or formula (II) directly to an individual who is in need of treatment for one or more of disorders that are typically treated by administration of cytidine (or a derivative thereof), suitable therapeutics are usually administered in the form of pharmaceutical compositions comprising a pharmaceutically acceptable excipient and at least one active ingredient. These compositions can be administered by a variety of routes including oral, rectal, transdermal, subcutaneous, intravenous, intramuscular, interperitoneal, and intranasal. Many of the compounds employed in the methods provided here are effective as both injectable and oral compositions. Such compositions are prepared in a manner well known in the pharmaceutical arts and comprise at least one active compound. See. e.g., REMINGTON'S PHARMACEUTICAL SCIENCES, (16th ed. 1980).

In making the therapeutic compositions disclosed herein, the active ingredient, which includes at least one compound having a formula in accordance with formula (I) or formula (II) is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill, crush, pulverize or grind the active compound to provide the appropriate particle size prior to combining with the other ingredients. If the active compound is substantially insoluble, it ordinarily is milled to a particle size of less than 200 mesh, more preferably less than 180 mesh, and most preferably less than 150 mesh. If the active compound is substantially water soluble, the particle size is normally adjusted by milling, crushing or grinding to provide a substantially uniform distribution in the formulation, e.g., about 40 mesh.

Some examples of suitable excipients include but are not limited to lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions can be formulated so as to provide quick, sustained or delayed release of the active ingredient after administration to an afflicted individual by employing procedures known in the art.

The compositions are preferably formulated in a unit dosage form, each dosage containing from about 0.05 to about 200 mg, more preferably about 1.0 to about 100 mg, and most preferably about 10 to 50 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.01 to about 50 mg/kg of body weight, more preferably about 0.1 to about 40 mg/kg of body weight, and most preferably about 1.0 to about 30 mg/kg of body weight. In the treatment of adult humans, the range of about 0.1 to about 20 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are exemplary and are not intended to limit the scope in any way. In some instances dosage levels below the lower limit of the aforesaid range may be more than adequate, while in other cases still larger doses may be employed without causing any harmful side effect, provided that such larger doses are first divided into several smaller doses for administration throughout the day or other suitable period. Thus, one skilled in the art given the benefit of this disclosure will be able to select suitable doses for administering to an individual in need of such treatment, e.g., for treatment of neoplastic syndromes and/or disorders. See, for example, those neoplastic diseases discussed in Section X of Goodman and Gilman's *The Pharmacological Basis of Therapeutics,* 9th Ed., 1996.

The compositions disclosed here may be useful for incorporating into genes to be delivered using gene therapy. In particular, substitution of one or more cytidines of the gene with pyrrolo-C or pyrrolo-dC provides for a functional gene, e.g., a gene that is capable of expressing an mRNA and/or protein under suitable conditions, and in addition provides for the added possibility of monitoring delivery of the gene using fluorescence measurements. Thus, a gene comprising one or more nucleosides comprising a composition in accordance with formula (II) can be introduced into an aberrant cell, e.g., a cell that does not have a normal functioning gene, to provide for expression of a desired protein. The efficiency of introducing the gene into the cell can be monitored or measured simultaneously or after introduction of the gene. Numerous methods for introducing genes into cells are known to those skilled in the art and include the use of bacteriophages, adenoviruses, adeno-associated viruses, retroviruses, lentiviruses and other suitable cells and carriers. One skilled in the art given the benefit of this disclosure will be able to select suitable cells and carriers for delivering one or more genes to treat a selected disorder.

A gene can be introduced into cells or a delivery device (such as a virus) prior to administration to a mammal (such as a human), or the gene can be introduced using other means. Various types of analysis, such as fluorescence microscopy, total internal reflection fluorescence microscopy, or fluorescence interference contrast microscopy, can be used to verify introduction of the gene into a cell. Because the fluorescence intensity of an introduced gene comprising one or more nucleosides comprising a composition in accordance with formula (II) is larger than genes comprising only naturally occurring nitrogenous bases, a gene including at least one nucleoside of formula (II) provides for a readily detectable signal within a cell. Thus, a small sample of cells, obtained, for example, through a biopsy, can be examined to determine if the gene was introduced into the cells. One skilled in the art, given the benefit of this disclosure, will be able to select suitable methods for determining the efficiency of gene delivery.

The fluorescent nitrogenous bases according to this disclosure, and nucleosides including the same, also may be used in the investigation of nucleic acid-nucleic acid interactions and in nucleic acid structure analysis. Without wishing to be bound by any particular scientific theory, it is believed that interaction of the fluorescent nitrogenous base disclosed here with one or more bases on a nucleic acid strand (either the same nucleic acid strand including the fluorescent nitrogenous base or a different nucleic acid strand) can alter the fluorescence properties of the fluorescent nitrogenous base, e.g., the fluorescence intensity, quantum yield, lifetime and/or rate constant may be increased or decreased. Thus, in embodiments in which a nucleic acid strand hybridizes to another nucleic acid strand, the change in the fluorescence of the nitrogenous base can provide information about the structure of the hybridized nucleic acid molecules. In certain examples, one or more reporters or quencher groups, e.g., one or more additional fluorescent molecules, is included in one or both of the nucleic acid strands. As the fluorescent nitrogenous base approaches such reporter or quencher groups, fluorescence resonance energy transfer may occur between the fluorescent nitrogenous base and the reporter or quencher group to alter the fluorescence of the fluorescent nitrogenous base. Because the change in fluorescence may be distance dependent (e.g., the distance between the fluorescent nitrogenous base and the reporter or quencher group can affect the degree in which the fluorescence changes), the change in fluorescence of the fluorescent nitrogenous base can be used as an indicator of structure of the nucleic acid-nucleic acid complex, e.g., secondary, tertiary or other structure. Numerous reporters and quenchers will be selected by those skilled in that art given the benefit of this disclosure. Exemplary reporters and quenchers can be obtained commercially from numerous manufacturers including, but not limited to: Molecular Probes (Eugene, Oreg.), IDT (Coralville, Iowa), Q-Biogene (Carlsbad, Calif.) and the like.

In certain examples, one or more radioactive nuclei, e.g., $^{32}$P, can be incorporated into a nucleic acid strand such that radioactive decay of the radioactive nuclei may provide the energy to excite the fluorescent nitrogenous base resulting in fluorescence emission. Other analytical techniques also may be used to determine the structure and properties of nucleic acids including the fluorescent nitrogenous base disclosed here, including but not limited to: mass spectroscopy, circular dichroism, electron paramagnetic resonance, nuclear magnetic resonance and/or X-ray crystallography, for example. One skilled in the art, given the benefit of this disclosure, will be able to select suitable techniques for investigating nucleic acid-nucleic acid interactions using the fluorescent nitrogenous bases disclosed here.

The fluorescent nitrogenous bases and nucleosides including the same disclosed herein also can be used in the investigation of nucleic acid-protein interactions and in the binding mechanisms of nucleic acids to proteins. Without wishing to be bound by any particular scientific theory, it is believed that interaction of the fluorescent nitrogenous base disclosed here with one or more amino acid residues of a protein can alter the fluorescence properties of the fluorescent nitrogenous base, e.g., the fluorescence intensity, quantum yield, lifetime and/or rate constant may be increased or decreased. Thus, in examples in which a nucleic acid strand binds to or associates with a protein, the change in the fluorescence of the nitrogenous base can provide information about the structure and nature of the nucleic acid-protein complex. In some examples, one or more reporters or quencher groups, e.g., one or more additional fluorescent molecules, may be included in the protein. In other examples, amino acids that have some intrinsic fluorescence (e.g., phenylalanine, tryptophan, tyrosine) can alter the fluorescence properties of the fluorescent nitrogenous base. For example, as the fluorescent nitrogenous base approaches such reporter or quencher groups, fluorescence resonance energy transfer may occur between the fluorescent nitrogenous base and the reporter or quencher group to alter the fluorescence of the fluorescent nitrogenous base. Because the change in fluorescence may be distance dependent, e.g., the distance between the fluorescent nitrogenous base and the reporter or quencher group can affect the degree in which the fluorescence changes, the change in fluorescence of the fluorescent nitrogenous base can be used as an indicator of structure of the nucleic acid-protein complex, e.g., secondary, tertiary, quaternary, or other structure. Exemplary reporters and quenchers can be obtained commercially from numerous manufacturers including those identified above.

In some examples, one or more radioactive nuclei (e.g., $^{32}$P, $^{35}$S, etc.), or in certain examples magnetically active nuclei (e.g., $^{15}$N, $^{19}$F), can be incorporated into an amino acid of the protein such that radioactive decay of the radioactive nuclei may provide the energy to excite the fluorescent nitrogenous base resulting in fluorescence emission. Other analytical techniques also may be used to determine the structure and properties of nucleic acid-protein complexes including the fluorescent nitrogenous base disclosed here, including but not limited to: mass spectroscopy, circular dichroism, electron paramagnetic resonance, nuclear magnetic resonance and/or X-ray crystallography, for example. One skilled in the art, given the benefit of this disclosure, will be able to select suitable techniques for investigating nucleic acid-protein interactions using the fluorescent nitrogenous bases disclosed here.

I. Specific Examples

Several examples demonstrating uses of the novel fluorescent base and nucleosides incorporating the same are described below. These examples serve to illustrate only a few of the numerous potential applications of the novel fluorescent bases and nucleosides including the same, and should not be construed as limiting the scope or content of the claims in any manner.

EXAMPLE 1

The general reaction scheme for this and several following examples is shown below:

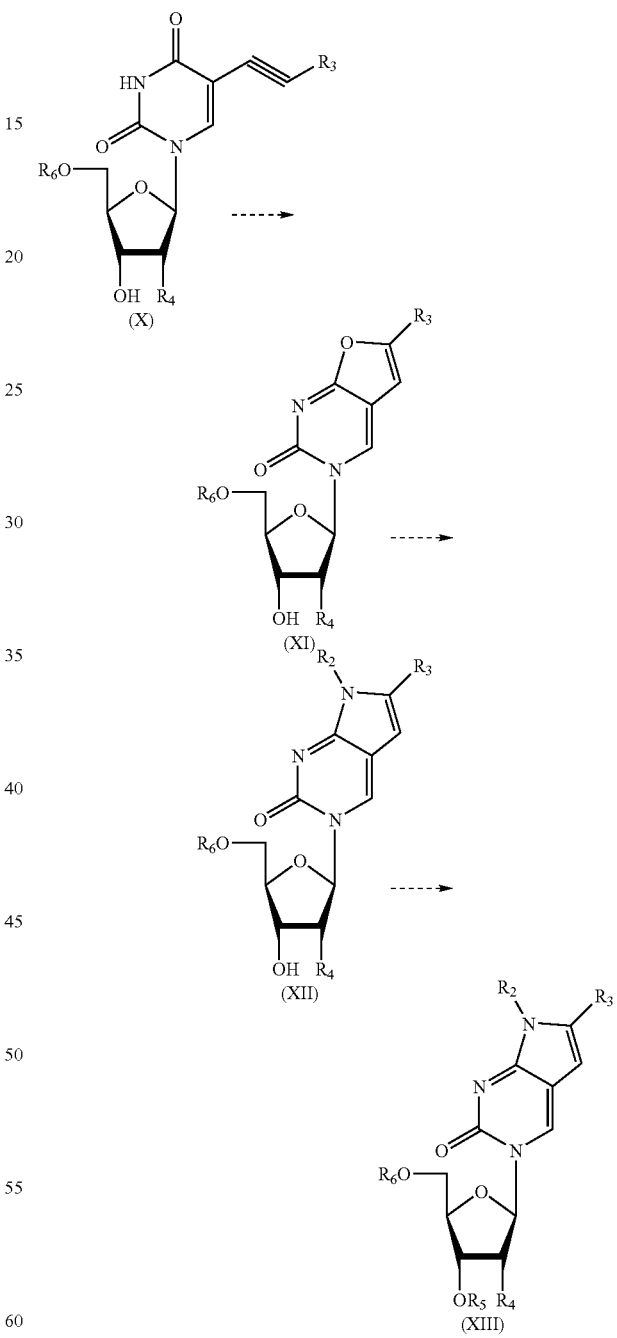

where $R_2$ represents hydrogen; $R_3$ represents a methyl group; $R_4$ represents hydrogen, a hydroxyl group, a protected hydroxyl group (e.g., a tert-butyldimethylsilyloxy group, a triisopropylsilyloxymethoxy group, or a 1-(2-fluorophenyl)-4-methoxypiperidin-4-yloxy group), fluorine, an allyloxy group, and a methoxy group; $R_5$ represents hydrogen, a 2-cyanoethoxy-N,N-diisopropylaminophosphinyl group, or a methoxy-N,N-diisopropylaminophosphinyl group; and $R_6$ represents hydrogen, a DMT (dimethoxytrityl) group or other 5'-protecting group (e.g., a monomethoxytrityl group, a pixyl group, or a 2-(2-nitrophenyl)propoxycarbonyl (nppoc) group), a phosphoryl group, or a triphosphoryl group.

Compounds of the type 6-Methyl-(3-β-D-2-($R_4$)-ribofuranosyl)-2,3-dihydrofuro[2,3-d]pyrimidin-2-one (XI) (where $R_6$=H and $R_4$=H,F, OH, OMe, O-allyl), were prepared by the general method described below.

Compounds having formula (X) obtained as described above (where $R_6$=H, and $R_4$=H, F, OH, O-Me, O-alkyl) (3 mmol) were added to 250 ml of anhydrous ammonia. 135 mL of triethylamine and 0.6 mmol of copper(I) iodide were added to this mixture. The mixtures were refluxed under a nitrogen atmosphere for 4–8 hours (depending on the starting material) or until thin layer monitoring of the reaction mixture indicated complete disappearance of the starting materials. The products were isolated in one of two ways. For the more hydrophobic products, the reaction mixture was concentrated in vacuo, and the remaining residue was partitioned between an organic phase (typically ethyl acetate or methylene chloride) and an aqueous solution of EDTA/sodium bicarbonate. The organic phase was dried over sodium sulfate, filtered, and concentrated in vacuo to afford the crude product. The product was then either recrystallized or purified by column chromatography. For those products that were considerably more polar, extraction was not feasible so the reaction mixture solution was adsorbed onto Florisil® ("Florisil®" is a synthetic magnesia-silica gel available from Mallinckrodt Chemicals) and loaded onto a column packed with Florisil®. Elution of the column with standard organic solvent pairs (dichloromethane/methanol) afforded the product fractions that were combined and concentrated in vacuo to afford the fluorescent compounds (XI) a–e (where $R_6$=H and $R_4$=H, F, OH, OMe, O-allyl), whose identities were verified by proton NMR and elemental analysis:

(XI)a, $R_6$=H, $R_4$=H (6-Methyl-3-(β-D-2-deoxyribofuranosyl)-2,3-dihydrofuro[2,3-d]pyrimidin-2-one);

(XI)b, $R_6$=H, $R_4$=F (6-Methyl-3-(β-D-2-deoxy-2-fluororibofuranosyl)-2,3-dihydrofuro[2,3-d]pyrimidin-2-one);

(XI)c, $R_6$=H, $R_4$=OH (6-Methyl-3-(β-D-ribofuranosyl)-2,3-dihydrofuro[2,3-d]pyrimidin-2-one;

(XI)d, $R_6$=H, $R_4$=O-Me (6-Methyl-3-(β-D-2-O-methylribofuranosyl)-2,3-dihydrofuro[2,3-d]pyrimidin-2-one); and (XI)e, $R_6$=H, $R_4$=O-allyl (6-Methyl-3-(β-D-2-O-allylribofuranosyl)-2,3-dihydrofuro[2,3-d]pyrimidin-2-one).

In some instances it was advantageous to carry out the ring closure on the appropriate 5'-O-dimethoxytritylated alkynyl starting material (X) (where $R_6$=DMT, $R_4$=H, F, OH, OMe, O-Allyl) to give 6-(Methyl-3-(β-D-5-O-(dimethoxytrityl)-2-(X)-ribofuranosyl)-2,3-dihydrofuro[2,3-d]pyrimidin-2-one's ((XI) f–j), following the general method described in Example 2 below.

EXAMPLE 2

The appropriate 5-alkynyl nucleoside (formula (X), where $R_6$=DMT, $R_4$=H, F, OH, OMe, O-Allyl) (3 mmol) was added to 250 ml of anhydrous methanol. To this mixture, 135 mL of triethylamine and 0.6 mmol of copper(I) iodide were added. The mixture was refluxed under a nitrogen atmosphere for 4–8 hours (depending on the starting material) or until thin layer monitoring of the reaction mixture indicated complete disappearance of the starting material. The reaction mixture was concentrated in vacuo, and the residue was partitioned between an organic phase (typically ethyl acetate or methylene chloride) and an aqueous solution of EDTA/sodium bicarbonate. The organic phase was dried over sodium sulfate, filtered, and concentrated in vacuo to afford the crude product.

The product was then either recrystallized or purified by column chromatography to afford the fluorescent compounds (XI) f–j (where $R_6$=DMT, $R_4$=H, F, OH, OMe, O-allyl). The identity of the products were verified by proton NMR, elemental analysis and fluorescence of the heterocycle:

(XI)f, $R_6$=DMT, $R_4$=H (6-Methyl-3-(5-O-dimethoxytrityl)-β-D-2-deoxyribofuranosyl)-2,3-dihydrofuro[2,3-d]pyrimidin-2-one);

(XI)g, $R_6$=DMT, $R_4$=F (6-Methyl-3-(5-O-dimethoxytrityl)-β-D-2-deoxy-2-fluororibofuranosyl)-2,3-dihydrofuro[2,3-d]pyrimidin-2-one);

(XI)h, $R_6$=DMT, $R_4$=OH (6-Methyl-3-(5-O-dimethoxytrityl)-β-D-ribofuranosyl)-2,3-dihydrofuro[2,3-d]pyrimidin-2-one);

(XI)i, $R_6$=DMT, $R_4$=O-Me (6-Methyl-3-(5-O-dimethoxytrityl)-β-D-2-O-methylribofuranosyl)-2,3-dihydrofuro[2,3-d]pyrimidin-2-one); and (XI)j, $R_6$=DMT, $R_4$=O-Allyl (6-Methyl-3-(5-O-dimethoxytrityl)-β-D-2-O-allylribofuranosyl)-2,3-dihydrofuro[2,3-d]pyrimidin-2-one).

The synthesis of the "pyrrolo-dC" analogs, (XII) a–j, were prepared from the appropriate starting materials (XI) a–j described above, where $R_6$=H or DMT and $R_4$=H, F, OH, O-Me, O-Allyl, following the general method described in Example 3.

EXAMPLE 3

The appropriate starting material (XI)a–j was dissolved in 7 M $NH_3$ in methanol and placed in a pressure vessel and heated at 55–60° C. for 3 days. The reaction vessel was cooled to 5° C. in an ice bath and then opened. The extent of the reaction was monitored by thin layer chromatography. If the reaction was incomplete, the reaction vessel was resealed and heated until the presence of starting material was no longer detectable. On a typical thin layer system of dichloromethane/methanol (10:1), the product ran slower than that of the starting material with both the starting material and product exhibiting fluorescence under long wavelength ultraviolet light. Once the reaction was deemed complete, as determined by thin layer chromatography, the reaction mixture was concentrated in vacuo to afford the crude product. These crude products were purified by either recrystallization or column chromatography to afford the fluorescent "pyrrolo-dC" title compounds (XII)a–j. Yields for (XII)a–j were typically in the range 60–70%, and the products were verified by proton NMR, elemental analysis and fluorescence of the heterocycle.

(XII)a, $R_6$=H, $R_4$=H (6-Methyl-3-(β-D-2-deoxyribofuranosyl)pyrrolo[2,3-d]pyrimidin-2-one);

(XII)b, $R_6$=H, $R_4$=F (6-Methyl-3-(β-D-2-deoxy-2-fluororibofuranosyl)pyrrolo[2,3-d]pyrimidin-2-one);

(XII)c, $R_6$=H, $R_4$=OH (6-Methyl-3-(β-D-ribofuranosyl)pyrrolo[2,3-d]pyrimidin-2-one;

(XII)d, $R_6$=H, $R_4$=O-Me (6-Methyl-3-(β-D-2-O-methylribofuranosyl)pyrrolo[2,3-d]pyrimidin-2-one);

(XII)e, $R_6$=H, $R_4$=O-allyl (6-Methyl-3-(β-D-2-O-allylribofuranosyl)pyrrolo[2,3-d]pyrimidin-2-one);

(XII)f, $R_6$=DMT, $R_4$=H (6-Methyl-3-(5-O-dimethoxytrityl)-β-D-2-deoxyribofuranosyl)-pyrrolo[2,3-d]pyrimidin-2-one);

(XII)g, $R_6$=DMT, $R_4$=F (6-Methyl-3-(5-O-dimethoxytrityl)-β-D-2-deoxy-2-fluororibofuranosyl)-pyrrolo[2,3-d]pyrimidin-2-one);

(XII)h, $R_6$=DMT, $R_4$=OH (6-Methyl-3-(5-O-dimethoxytrityl)-β-D-ribofuranosyl)pyrrolo-[2,3-d]pyrimidin-2-one;

(XII)i, $R_6$=DMT, $R_4$=O-Me (6-Methyl-3-(5-O-dimethoxytrityl)-β-D-2-O-methylribo-furanosyl)pyrrolo[2,3-d]pyrimidin-2-one); and (XII)j, $R_6$=DMT, $R_4$=O-Allyl (6-Methyl-3-(5-O-dimethoxytrityl)-β-D-2-O-allylribofuranosyl)pyrrolo[2,3-d]pyrimidin-2-one).

For incorporation of "pyrrolo-dC" analogs into DNA or RNA via appropriate synthesizer instruments, it was first necessary to prepare 3'-O-phosphoramidites, either as the O-methyl or O-(2-cyanoethyl) versions. The phosphoramidite products 6-(Methyl)-3-(β-D-2-($R_4$)-5-O-DMT-3-($R_2$)-ribofuranosyl)pyrrolo[2,3-d]pyrimidin-2-one (where $R_6$=DMT, $R_5$=methyl or 2-cyanoethyl, and $R_4$=H, F, OY, O-Me, O-allyl; where Y=TBDMS, TOM or other 2'-protecting group) (Compound (XIII)) were prepared by the general method described in Example 4.

EXAMPLE 4

The appropriate starting material (XII)f–j (2 mmol) was dissolved in 35 ml of anhydrous dichloromethane. The appropriate phosphitylating agent, as the bis(N,N-diisopropylamino) form, was added to this solution followed by 0.4 equivalents of tetrazole. The reaction was stirred at room temperature for 4–8 hours, or until disappearance of the starting material was observed by thin layer chromatography. To get an accurate interpretation of the extent of reaction, deactivation of the thin layer plate with triethylamine prior to spotting the reaction mixture was necessary. Once the reaction was completed, the reaction mixture was washed with 5% aqueous sodium bicarbonate, and the organic layer was dried over sodium sulfate. Before washing the reaction mixture with aqueous sodium bicarbonate, both the reaction mixture and bicarbonate wash were cooled in an ice bath. After removal of the drying agent, the organic layer was concentrated in vacuo (10 torr, 30° C.) to afford a resinous product. Flash column purification with typical organic solvent mixtures (dichloromethane/methanol/TEA or Ethyl Acetate/Hexanes/TEA) afforded the "pyrrolo-dC" title compounds (XIII)f–o (where $R_6$=DMT, $R_5$=2-cyanoethyl or methyl and $R_4$=H, F, O-Me, O-allyl), and the resulting products were identified by proton NMR and elemental analysis.

(XIII)f, $R_6$=DMT, $R_4$=H, $R_5$=2-cyanoethyl (6-Methyl-3-(5-O-dimethoxytrityl)-β-D-2-deoxyribofuranosyl)pyrrolo[2,3-d]pyrimidin-2-one 3'-O-[(2-Cyanoethyl) N,N-diisopropyl]phosphoramidite);

(XIII)g, $R_6$=DMT, $R_4$=F, $R_5$=2-cyanoethyl (6-Methyl-3-(5-O-dimethoxytrityl)-β-D-2-deoxy-2-fluororibofuranosyl) pyrrolo[2,3-d]pyrimidin-2-one 3'-O-[(2-Cyanoethyl) N,N-diisopropyl]phosphoramidite);

(XIII)h, $R_6$=DMT, $R_4$=OY, $R_5$=2-cyanoethyl (6-Methyl-3-(5-O-dimethoxytrityl)-β-D-ribofuranosyl)pyrrolo[2,3-d]pyrimidin-2-one 2'-OY 3'-O-[(2-Cyanoethyl) N,N-diisopropyl]phosphoramidite), where Y=TBDMS, TOM or other 2'-protecting group;

(XIII)i, $R_6$=DMT, $R_4$=O-Me, $R_5$=2-cyanoethyl (6-Methyl-3-(5-O-dimethoxytrityl)-β-D-2-O-methylribofuranosyl) pyrrolo[2,3-d]pyrimidin-2-one 3'-O-[(2-Cyanoethyl) N,N-diisopropyl]phosphoramidite);

(XIII)j, $R_6$=DMT, $R_4$=O-Allyl, $R_5$=2-cyanoethyl (6-Methyl-3-(5-O-dimethoxytrityl)-β-D-2-O-allylribofuranosyl)pyrrolo[2,3-d]pyrimidin-2-one 3'-O-[(2-Cyanoethyl) N,N-diisopropyl]phosphoramidite);

(XIII)k, $R_6$=DMT, $R_4$=H, $R_5$=methyl, (6-Methyl-3-(5-O-dimethoxytrityl)-β-D-2-deoxyribofuranosyl)pyrrolo[2,3-d]pyrimidin-2-one 3'-O-(Methyl-N,N-diisopropyl)phosphoramidite);

(XIII)l, $R_6$=DMT, $R_4$=F, $R_5$=methyl (6-Methyl-3-(5-O-dimethoxytrityl)-β-D-2-deoxy-2-fluororibofuranosyl) pyrrolo[2,3-d]pyrimidin-2-one 3'-O-(Methyl-N,N-diisopropyl)phosphoramidite);

(XIII)m, $R_6$=DMT, $R_4$=OY, $R_5$=methyl (6-Methyl-3-(5-O-dimethoxytrityl)-β-D-ribofuranosyl) pyrrolo[2,3-d]pyrimidin-2-one 2'-OY 3'-O-(Methyl-N,N-diisopropyl)phosphoramidite), where Y=TBDMS, TOM or other 2'-protecting group;

(XIII)n, $R_6$=DMT, $R_4$=O-Me, $R_5$=methyl (6-Methyl-3-(5-O-dimethoxytrityl)-β-D-2-O-methylribofuranosyl)pyrrolo[2,3-d]pyrimidin-2-one 3'-O-(Methyl-N,N-diisopropyl)phosphoramidite); and (XIII)o, $R_6$=DMT, $R_4$=O-Allyl, $R_5$=methyl (6-Methyl-3-(5-O-dimethoxytrityl)-β-D-2-O-allylribofuranosyl)pyrrolo [2,3-d]pyrimidin-2-one 3'-O-(Methyl-N,N-diisopropyl) phosphoramidite).

Pyrrolo-dC and analogous phosphoramidites are readily incorporated into oligonucleotides using standard phosphoramidite chemistry without requiring any modification of the coupling time or the DNA synthesis cycle. Oxidation and deprotection can be accomplished using 0.02 M $I_2$ for oxidation and room temperature deprotection in 30% $NH_4OH$. Pyrrolo-dC is completely compatible with Beaucage Sulfurizing Reagent, allowing facile synthesis of phosphorothioate oligos.

Generally speaking, DNA or RNA automated synthesizers are the chosen methods for the incorporation of specific individual bases into DNA or RNA. However, molecular biologists sometimes prefer to utilize biochemical means to accomplish this task, or to study cellular DNA or RNA mechanistics. For this use, either the 5'-phosphate or triphosphate of the nucleoside is required. To this end, the 5'-phosphates and triphosphates were prepared by routine literature methods to afford the title compounds, (XIII) (where $R_6$=phosphoryl, triphosphoryl, $R_5$=H and $R_4$=H, F, OH, methoxy, allyloxy, alkynylalkoxy, aminoalkyloxy, or an aminoalkoxy group wherein the amino group bears a protecting group). Without wishing to be bound by any particular scientific theory, these various derivatives of the fluorescent pyrrolo-dC or pyrrolo-C should allow for exploration of the mechanisms of a broad range of DNA/RNA cellular and intracellular activities using fluorescence techniques.

EXAMPLE 5

The spectral properties of pyrrolo-dC, coupled with its unique base-pairing ability, make this fluorescent analog extremely valuable in probing DNA structure. When the pyrrolo-dC is base-paired, its fluorescence can be reduced or quenched through what is most likely base stacking interactions (see Table I).

TABLE I

|  | E260 (L/mol cm) | $E_{345}$ (L/mol cm) | QY |
| --- | --- | --- | --- |
| Pyrrolo-dC | 4,000 | 3,700 | 0.07 single-stranded 0.02 double-stranded |

(QY - quantum yield; determined relative to quinine sulfate in O.5 M $H_2SO_4$)

The quantum yield of fluorescence for pyrrolo-dC is quite sensitive to its hybridization state, making it ideally suited for probing the dynamic structure of DNA. Work by Liu and Martin (see C. Liu and C. T. Martin, J Biol Chem, 2002, 277, 2725–31) has shown that when the pyrrolo-dC is mismatched in an otherwise duplex hybrid, the fluorescence is higher than the single-stranded species when the mismatched base is adenosine. This most likely arises from efficient energy transfer from the adenosine to the pyrrolo-dC. This unusual behavior also allows differentiation in situ between a DNA-DNA duplex and a DNA-RNA heteroduplex.

EXAMPLE 6

The quenching of pyrrolo-dC allows local structural changes to be probed with great sensitivity. Using pyrrolo-dC, Liu and Martin (Liu, C. and Martin, C. T., J Mol Biol, 2001, 308, 465–75) have characterized the transcription bubble in elongation complexes of T7 RNA Polymerase to single-base resolution by observing roughly a two-fold increase in fluorescence as the polymerase induces melting. By starving the T7 RNA Polymerase of specific nucleoside triphosphates, the enzyme could be stalled at specific sites, producing 'fluorescence snapshots' of the complex, and yielding detailed information on the nature of the transcription bubble and heteroduplex.

EXAMPLE 7

The hybridization specificity of pyrrolo-dC was evaluated by determining the melting temperature ($T_m$) of a 19 mer oligonucleotide with the sequence 5'-GCC TAA CTT CXG GAG ATG T-3' (SEQ ID NO.: 1), where X is Pyrrolo-dC which contains a single pyrrolo-dC. This oligonucleotide was annealed to complementary strands containing each of the four natural deoxyribonucleotide bases opposite it. Hybridization was best with a strand containing dG opposite pyrrolo-dC and decreased in the order dG>dT>dA>dC (melting temperature $T_m$=65, 56, 55 and 52° C. respectively). The effect of multiple incorporations was next evaluated by synthesizing a T7 universal primer where dC was replaced with zero to four pyrrolo-dC residues. All five oligonucleotides had the same $T_m$ as that of the control (57° C.) when hybridized with an oligonucleotide complementary to the T7 primer regardless of the number of pyrrolo-dC/dC substitutions. Thus, substitution of dC with pyrrolo-dC did not significantly affect the melting temperature of the DNA complex.

EXAMPLE 8

A series of tests were performed to test the ability of the T7 primers synthesized above to function in biological assays. In the first series of tests each of the T7 primers was evaluated in a PCR assay for their ability to amplify a plasmid insert. In the first experiment either the control or one of the experimental T7 forward primers, with one to four pyrrolo-dC substitutions, and an Sp6 reverse primer were tested for their ability to amplify a plasmid 600-nucleotide insert using supramaximal primer concentrations and the PCR products analyzed on an acrylamide gel. The sequences of the T7 forward primers are as follows: 5'-TAA TAC GAX TCA CTA TAG G-3' (SEQ ID NO.: 6); 5'-TAA TAC GAX TXA CTA TAG G-3' (SEQ ID NO.: 7); 5'-TAA TAX GAX TXA CTA TAG G-3' (SEQ ID NO.: 8); 5'-TAA TAX GAX TXA XTA TAG G-3' (SEQ ID NO.: 9); (control) 5'-TAA TAC GAC TCA CTA TAG G-3' (SEQ ID NO.: 10), where X=pyrrolo-dC. Analysis of the stained gel was consistent with no differences in either the mobility or intensity of the stained bands corresponding to the 600-nucleotide PCR product generated by the control or experimental T7 primers.

The control and experimental T7 primers were next compared in another experiment using limiting concentrations of each of the T7 primers (1.3, 0.4, 0.15 and 0.05 pmole per reaction) and excess Sp6 primer. Analysis of the stained gels showed the same concentration dependent pattern of product band between the control and experimental samples indicating that primers containing pyrrolo-dC substitutions were used with the same efficiency as those containing dC. Finally the control and T7 primer containing four pyrrolo-dC substitutions were compared in their ability to be recognized by a variety of polymerases, Taq from ABI, Vent from New England Biolabs and Pfu from Stratagene. In this case a biotinylated Sp6 primer was used as the reverse primer in the amplification reaction of a plasmid containing an approximately 500 nucleotide insert. All reactions showed that there was equivalence between the experimental T7 primer containing four pyrrolo-dC substitutions SEQ ID NO.:6, SEQ ID NO.:7, SEQ ID NO.:8, SEQ ID NO.:9 and the unsubstituted version, with Vent showing a lower efficiency of production of the ~500 nucleotide fragment, for both the unsubstituted and pyrrolo-dC substituted primers, compared to the other two polymerases.

EXAMPLE 9

A series of tests was designed to determine if a pyrrolo-dC residue coded as dC for a dG. In this experiment a 100× diluted aliquot of the ~500 nucleotide insert generated by the control T7 and Sp6 primers was further amplified using a biotinylated Sp6 primer and either a control 42 base M13-T7 primer or one with four pyrrolo-dC substitutions in the T7 sequence. The PCR product was captured on streptavidin beads, excess primers were removed by washing, and the suspension was divided into two portions. One reaction (the antisense strand) was sequenced using an M13 forward primer (using ABI dRhodamine chemistry); the other was sequenced (carried out using Beckman dye terminator chemistry) by using Sp6, after releasing the sense strand by heat denaturation of the immobilized PCR fragment. In all cases, wherever a pyrrolo-dC had been substituted, the sequence showed a C in the sense strand extension product or a G in the antisense strand product at the corresponding position. Therefore, under cycle sequencing conditions, the pyrrolo-dC residue is "read" as a dC.

EXAMPLE 10

The triphosphate of pyrrolo-dC (pyrrolo-dCTP) was synthesized and compared with dCTP for its ability to be recognized by polymerases and be incorporated as a dC into polymerase generated products. Nucleotide-triphosphate mixes containing either dCTP or pyrrolo-dCTP were used in amplification reactions similar to the ones above and the product analyzed by acrylamide gel. There was no discernable difference in the intensity or mobility of bands corresponding to the amplified insert indicating that the triphosphate of pyrrolo-dC was recognized and incorporated with the same efficiency as dCTP. Additionally when the PCR generated product was sequenced it was shown that pyrrolo-dC was specifically incorporated as a "dC" opposite a dG residue.

EXAMPLE 11

Figure 4:
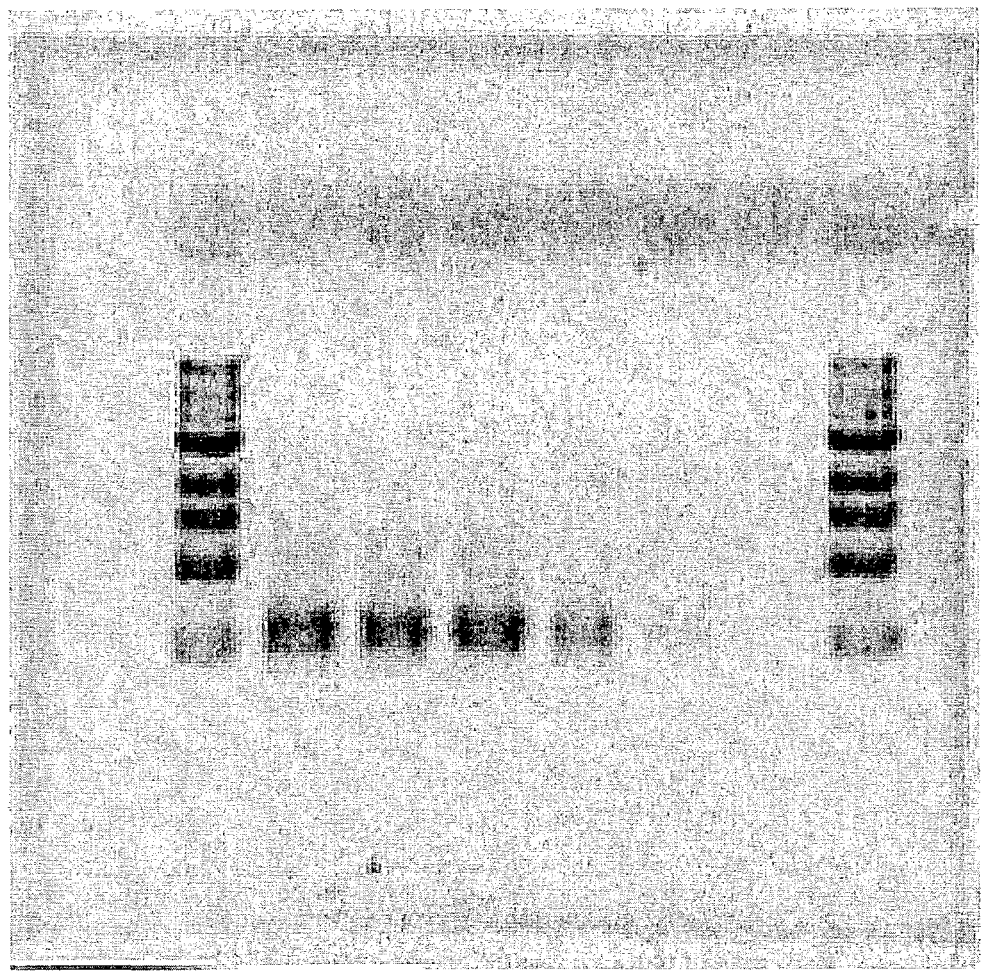
FIG. 4 is a gel showing the results of primer dilution studies using pyrrolo-dC-substituted and unsubstituted T7 primers in which the most highly substituted pyrrolo-dC primer was used to establish the range of primer concentration over which a PCR fragment could be produced. Lane 1 shows 4 pmole T7 control, Lanes 2–6 show bands where 4, 1.3, 0.4, 0.15 and 0.05 pmole of pyrrolo-dC T7 primer were used.

Studies on primers including pyrrolo-dC were performed to identify supramaximal amounts of primers Sp6 and T7 (and related substitutions) using a plasmid with a 600- nucleotide insert. This example was performed to determine if the congeners are equally effective at priming the reaction by using a diluting series. The results are shown in FIG. 4. Primer dilution studies were carried out to examine the effectiveness of the T7 primers that were substituted with different numbers of pyrrolo-dC. The primer most highly substituted with pyrrolo-dC (SEQ ID NO.:9) was used to establish the range of primer concentration over which the PCR fragment could be produced (see FIG. 4); the leftmost lane shows 4 pmol T7, those to the right were 4, 1.3, 0.4, 0.15 and 0.05 pmol of pyrrolo-dC T7, with a sharp decrease in product formation around 0.15 pmol. All substituted T7 primers functioned similarly as the unsubstituted T7 primers.

EXAMPLE 12

Figure 5A:
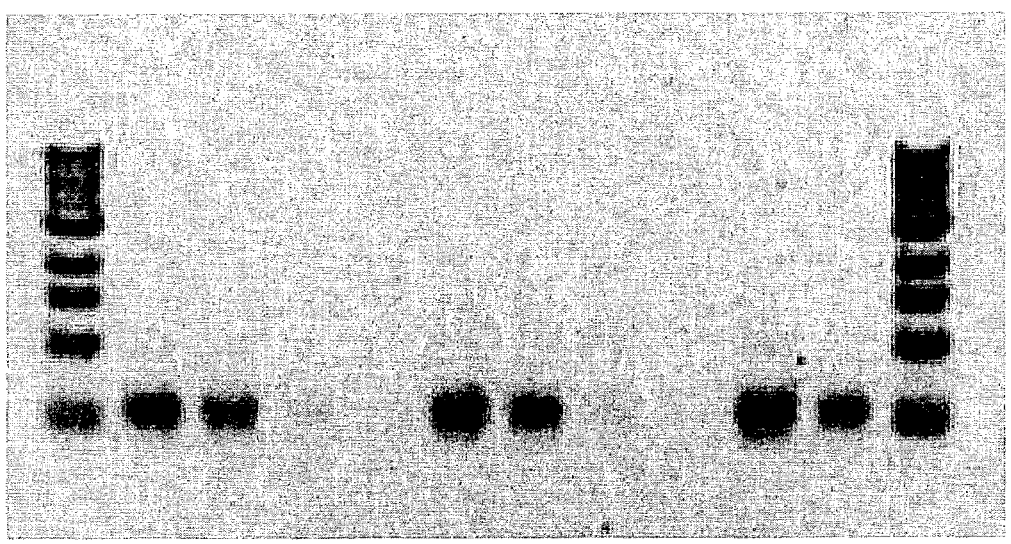
FIGS. 5A and 5B are gels showing the results of substituted pyrrolo-dC and unsubstituted T7 primers using primer amounts of 1.3, 0.4, 0.15 and 0.05 pmole per reaction. Lanes 1 and 12 of FIGS. 5A & 5B MWM markers. For reference, the sets of 4 (starting with the upper left) were 4, 3, 2, 1 and 0 pyrrolo-dC substitutions.
Figure 5B:
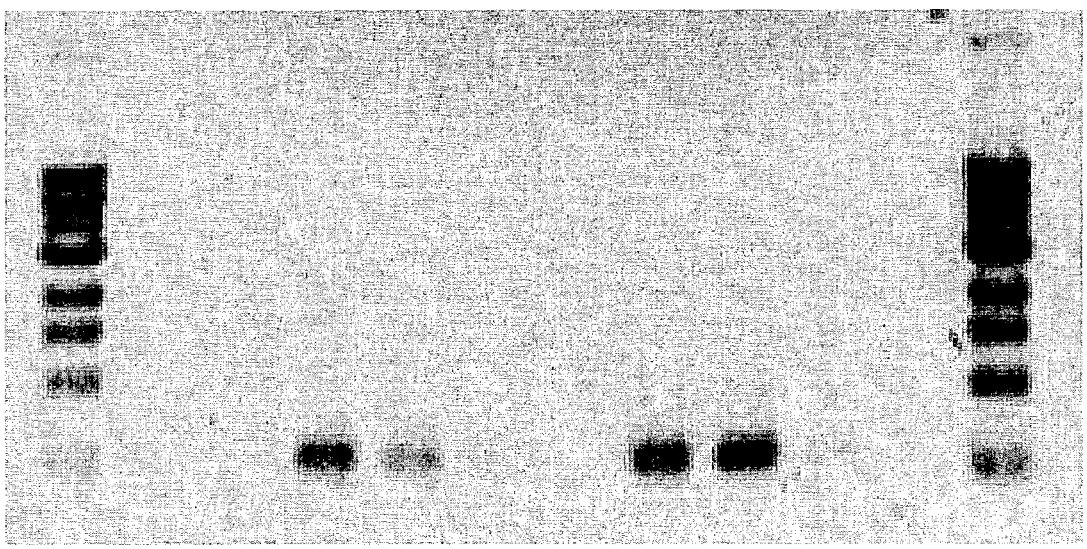

Primers substituted with pyrrolo-dC were tested to determine if the primers exhibited a similar concentration dependence as control primers. All of the analogs were compared with the unsubstituted T7 using primer amounts of 1.3, 0.4, 0.15 and 0.05 pmol per reaction. There were no discernable differences in these sets, indicating that the pyrrolo-dC substituted analogs behaved identically to the unsubstituted T7 (see FIGS. 5A and 5B). For reference purposes, the sets of 4 (starting with the upper left) were 4, 3, 2, 1 and 0 pyrrolo-dC substitutions. Any differences observed are believed to be minor dilution or photographic differences.

EXAMPLE 13

Figure 6:
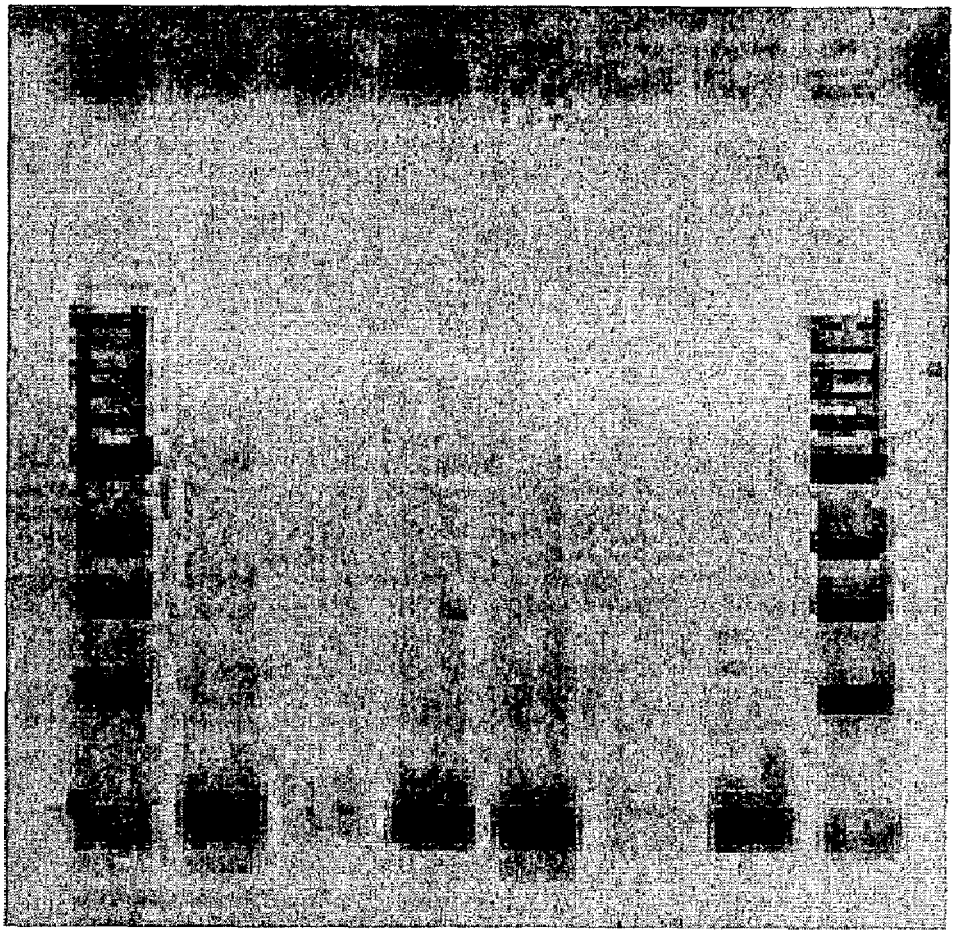
FIG. 6 is a gel showing the effects of substituted pyrrolo-dC primers on the activity of several polymerases. Lane 1 is standards, lane 2 is T7-4 pdC primer with Taq (ABI), lane 3 is T7-4 pdC primer with Vent (NEB), lane 4 is T7-4 pdC primer with Pfu (Stratagene), lane 5 is T7 primer with Taq (ABI), lane 6 is T7 primer with Vent (NEB), lane 7 is T7 primer with Pfu (Stratagene); and lane 8 standards.

Experiments were carried out to examine the effect of substituted pyrrolo-dC primers on the activity of several polymerases. Three experiments were carried out to examine the ability of different polymerases (Taq, Vent, Pfu) to use the T7 or T7-4 pyrrolo-dC primer in PCR; the other primer in the pair was biotinylated Sp6. All reactions showed that there was equivalence between the T7-4 pyrrolo-dC primer and the unsubstituted version, with Vent showing a lower efficiency of production of the ~500 nucleotide fragment compared to the other two polymerases; Vent (and other proof-reading polymerases) are often less robust and require optimization of reaction conditions to get best results. FIG. 4 shows the results of the experiments. In FIG. 6, lane 1 is standards, lane 2 is T7-4 pyrrolo-dC primer with Taq (ABI), lane 3 is T7-4 pyrrolo-dC primer with Vent (NEB), lane 4 is T7-4 pyrrolo-dC primer with Pfu (Stratagene), lane 5 is T7 primer with Taq (ABI), lane 6 is T7 primer with Vent (NEB), lane 7 is T7 primer with Pfu (Stratagene), and lane 8 is standards.

EXAMPLE 14

Sequencing reactions (in duplicate) were carried out with PCR fragments to determine if pyrrolo-dC substitutes for dC. PCR fragments were generated by using, as template, a 100-fold dilution of the product of T7/bio-Sp6 reaction (similar to lane 5 above) and a primer pair of biotinylated Sp6 and the M13F-T7 (or its pyrrolo-dC-substituted homolog). The PCR fragment from this amplification was purified by streptavidin beads to remove excess primers and the suspension divided into two portions. One reaction (the antisense strand) was sequenced using M13 F (using ABI dRhodamine chemistry); the other was sequenced (carried out using Beckman dye terminator chemistry) by using Sp6, after releasing the sense strand by heat denaturation of the immobilized PCR fragment. In all cases, wherever a pyrrolo-dC had been substituted, the sequence showed a C in the sense strand extension product or a G in the antisense strand product at the corresponding position. Thus, under cycle sequencing conditions, the pyrrolo-dC residue is read as a dC. These data demonstrate comparability (with respect to polymerases) of pyrrolo-dC when it has been incorporated synthetically into a primer, both in terms of efficiency and in terms of recognition as a C residue.

EXAMPLE 15

Figure 7:
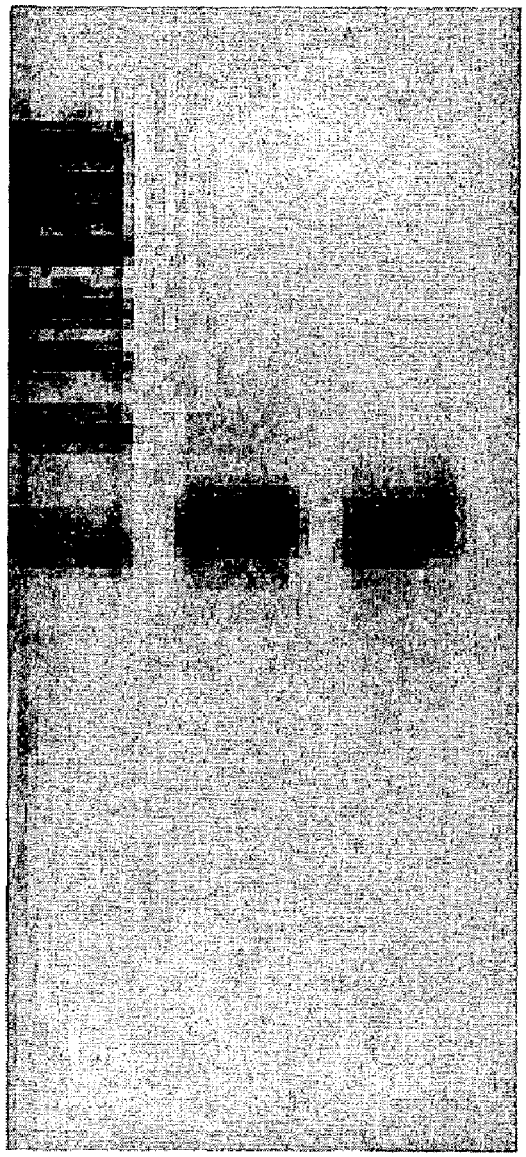
FIG. 7 and FIG. 8 each show purified plasmid DNA with 500–600 bp inserts that were amplified in a standard 25 µl PCR reaction.
Figure 8:
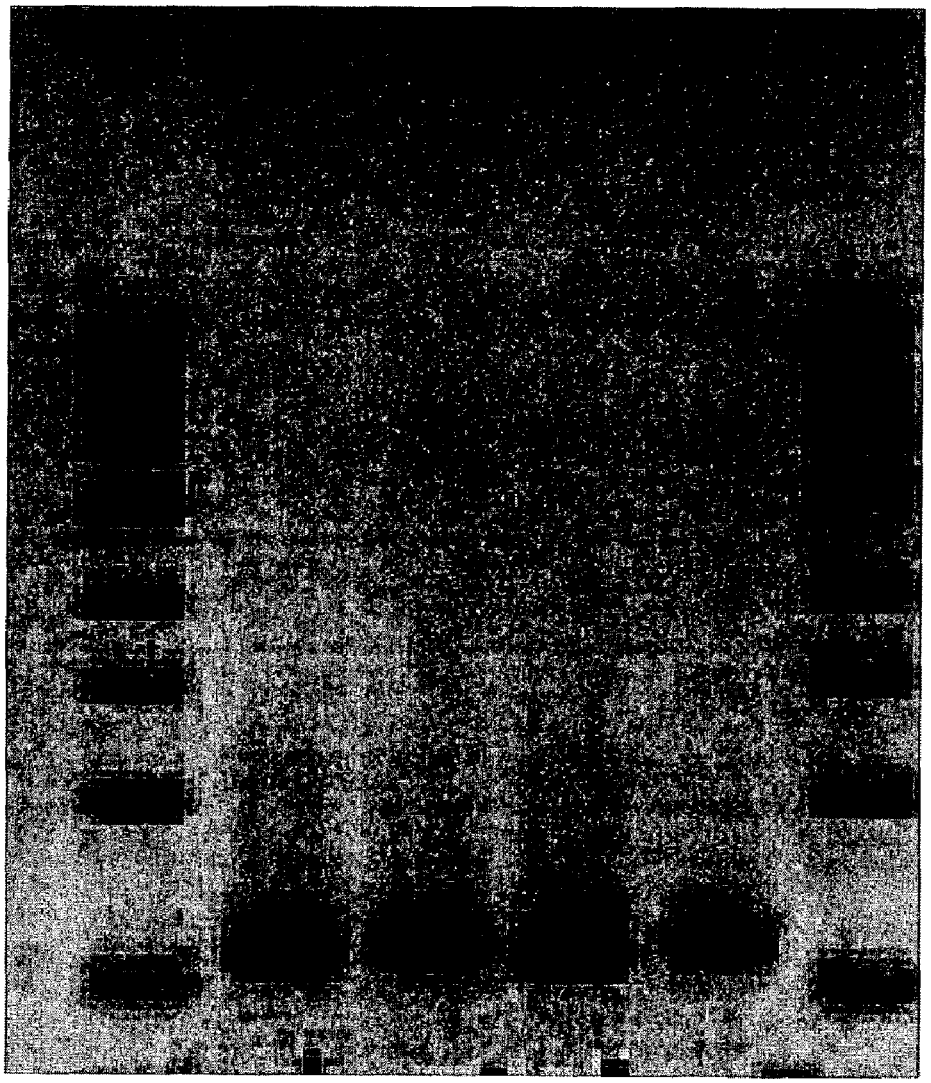

The PCR and sequencing experiments in Example 15 were repeated to determine if polymerases incorporated pyrrolo-dCTP as efficiently as dCTP (FIGS. 7 & 8). Purified plasmid DNA with 500–600 bp inserts were amplified in a standard 25 µl PCR reaction. One of the primers was biotinylated to facilitate the post-reaction cleanup of the PCR product. AmpiTaq DNA polymerase (1.25 Units, Applied Biosystems) was used as enzyme with 200 µM final concentration of each dNTP. In the pyrrolo-dCTP samples the dCTP was replaced with 200 µM pyrrolo-dCTP. Following the PCR reaction (55° C. annealing for 20 sec, 72° C. extension for 45 sec, 30 cycles) an aliquot of the reaction was subjected to agarose gel electrophoresis to verify the size and quality of the product. The biotinylated PCR product was purified by streptavidin-coated magnetic beads. An aliquot of the purified product, still attached to the magnetic beads, was sequenced in a standard fluorescent dye-terminator cycle sequencing reaction and analyzed on a Beckman CEQ2000XL DNA sequencer.

A PCR product, with size and intensity similar to the control, was produced in every case when the dCTP was replaced with the pyrrolo-CTP derivative (see FIGS. 7&8). This clearly indicates that the polymerase can incorporate the pyrrolo congener.

The sequencing results confirm the above observations that pyrrolo-dCTP substituted samples show the same sequence as the control, both pyrrolo-dC's and dC's are read correctly as C, however, the signal intensity is lower, with lot of "noise" and the sequence appears to be slightly mixed in most cases, which suggests the presence of multiple molecular species. This is consistent with an inhomogeneous PCR product, which is not necessarily unexpected due to AmpiTaq polymerase's lack of any proofreading activity.

EXAMPLE 16

Figure 9:
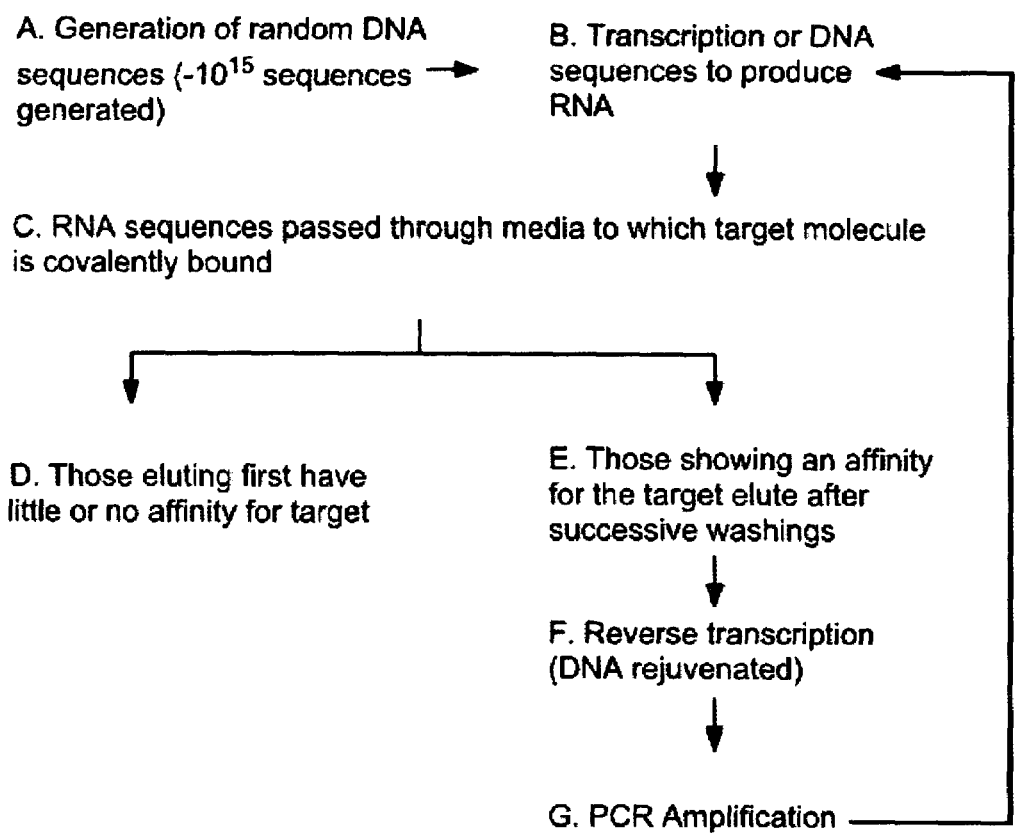
FIG. 9 shows a diagram of Systematic Evolution of Ligands through EXponential amplification (SELEX).

One or more pyrrolo-C and/or pyrrolo-dC molecules can be used in aptamers or ribozymes. While it was initially believed that only proteins which possess 20 monomeric building blocks were capable of generating the structural diversity required for high affinity ligand binding, that view changed in 1990 when Ellington and Szostak and, shortly thereafter Turek and Gold, published papers describing RNA molecules that bound to dyes and proteins respectively with high affinity. See, for example, Ellington, A. D. and Szostak, J. W., *Nature,* 1990, 346, 818–822 and Tuerk, C. and Gold, L. *Science,* 1990, 249, 505–510. Initial binding affinities were not as high as those observed in antibody antigen interactions, however it was possible to rapidly "mature" the RNA molecules into higher affinity binders though a process called Systematic Evolution of Ligands through EXponential amplification (SELEX). See. FIG. 9.

Subsequent work has shown that aptamers are not limited to RNA and that DNA aptamers also work well. See, for example, Breaker, R. R. *Nat Biotechnol,* 1999, 17, 422–423 and Joyce, G. F. Proc Natl Acad Sci USA, 1998, 95, 5845–5847. In fact, aptamers containing only two bases (e.g., pyrrolo-dC or pyrrolo-C and Uracil) can be developed that bind to various targets. See, for example, Reader, J. S., and Joyce, G. F. *Nature,* 2002, 420, 841–844. Thus, providing a greater assortment of monomers, e.g., pyrrolo-dC, allows for development of higher affinity aptamers.

Not content with mere ligand binders, a number of groups developed RNAs that had catalytic properties. The SELEX procedure was used, usually in conjunction with a clever way of "catching" those RNAs with enzymatic activity. It was known at the time, that only the RNA component of the bacterial RNAse P was required for enzymatic activity although the presence of the protein scaffold dramatically improved kinetics. See, for example, James, B. D., Olsen, G. J., Liu, J. S., and Pace, N. R. Cell, 1988, 52, 19–26. Like the RNAse P example, in vitro selected ribozymes were nowhere near as catalytically active as proteins. That said, ribozymes were developed to catalyze some interesting reactions. One ribozyme was designed to catalyze a Diels-Alder reaction (although modified bases were required). See, for example, Tarasow, T. M., Tarasow, S. L., and Eaton, B. E. Nature, 1997, 389, 54–57 and Morris, K. N., Tarasow, T. M., Julin, C. M., Simons, S. L., Hilvert, D., and Gold, L. Proc Natl Acad Sci USA, 1994, 91, 13028–13032. DNAzymes have also been developed. See, for example, Cairns, M. J., Hopkins, T. M., Witherington, C., Wang, L., and Sun, L. Q. Nat Biotechnol., 1999, 17, 480–486

SELEX (see FIG. 9) begins with a ligand of interest such as, for example, vitamin B12. A library of chemically synthesized DNAs, comprising one or more pyrrolo-dC for example, consisting of about $10^{15}$ members is synthesized chemically. This library is then transcribed with a viral RNA polymerase, typically T7, to generate a population of single stranded RNAs. Pyrrolo-C can be provided such that the transcribed single stranded RNAs contain one or more pyrrolo-C molecules. The RNAs are then applied to an immobilized ligand and washed to remove low affinity binders. The remaining RNAs are eluted, amplified by RT-PCR and the process begins again. Pyrrolo-C can be incorporated into the amplified RNAs by providing pyrrolo-C in the reaction mixtures. Typically 5 cycles are required to obtain high affinity binders. This population is cloned and sequenced. From the sequence data, one learns which residues are important for binding and which are not. The power of SELEX comes from coupling affinity purification and PCR amplification.

A desirable application is making RNA drugs that bind to and inhibit specific proteins. The problem with this approach is that RNAs can be very unstable in body fluids. RNAs can be modified to increase their nuclease stability. Another application is to use aptamers in the place of antibodies in clinical diagnostics and protein chip array technology. See, for example, Hesselberth, J., Robertson, M. P., Jhaveri, S., and Ellington, A. D. J. Biotechnol., 2000, 74, 15–25 and Jhaveri, S., Rajendran, M., and Ellington, A. D. Nat. Biotechnol., 2000, 18, 1293–1297. Finally, aptamers may be useful as catalysts of chemical reactions.

As diagnostic agents, aptamers possess some distinct advantages one of which is that they undergo a conformational change upon ligand binding. By incorporating well positioned fluorophores, such as pyrrolo-dC, pyrrolo-C or both, one can infer the presence and extent of ligand binding by monitoring changes in resonance energy transfer or other suitable fluorescence parameters, e.g., fluorescence rate constants, lifetime, emitted photons, etc.

Numerous methodologies for making ribozymes and aptamers will be selected by those skilled in the art, given the benefit of this disclosure, and exemplary techniques include but are not limited to those methods discussed in, for example, U.S. Pat. Nos. 6,524,853, 6,475,998, 5,225,337, 5,144,019, 5,582,981, 5,756,291, 5,840,867, 6,458,559, 6,509,460, 6,511,809, and 6,515,120, the entire disclosure of each of which is incorporated herein in its entirety by reference.

In other examples the groups that form the backbone of polynucleotides including pyrrolo-C and/or pyrrolo-dC can be modified using suitable methodologies that are known to those skilled in the art. That is, the groups, e.g., sugars, that make up the backbone of nucleic acids can be modified in accordance with suitable techniques that are known to those skilled in the art. Such modifications include, but are not limited, to replacement of the phosphodiester group or the whole sugar phosphodiesters with alternative anionic, cationic or neutral groups. Other modifications include, for example, 2'-O modifications, heterocyclic base modifications, sugar modifications, replacement of 3'-OH with 3'-amino, replacement of the sugar backbone with synthetic peptide backbones, e.g., those formed of N-(2-amino-ethyl)-glycine units, to form peptide nucleic acids (PNAs), modifications to form locked nucleic acids (LNAs) such as modification constraining the sugar moiety by a suitable linkage, e.g., a methylene linkage between the 2'-oxygen and the 4'-carbon, modifications to form ethylene-bridged nucleic acids (ENAs), such as modification to form 2'-O-4'-C-ethylene nucleosides, and the like. Exemplary techniques for modifying nucleic acids include, but are not limited to, the methods discussed in Micklefield, J. Curr. Medicinal Chemistry, 2001, 8, 1157–1179; Freier and Altman, Nucleic Acids Res., 1997, 25, 4439–43; Gryaznov, S M, Biochim Biophys. Acta, 1999, 1489, 131–40; Rait et al., Nucleosides Nucleotides, 1999, 18, 1379–80; Ray et al., FASEB J., 2000, 14, 1041–60; Braasch et al., Chem. Biol., 2001, 8, 1–7; and Hasegawa et al., Bioorg Med. Chem. Lett., 2002, 12, 73–6. Other suitable techniques for modifying polynucleotide backbone structures will be recognized by those skilled in the art given the benefit of this disclosure.

Although certain examples are described above, it will be recognized by those skilled in the art, given the benefit of this disclosure, that numerous other aspects, embodiments, alterations, modification, and substitutions are possible. It is intended that the following claims be read as covering such alterations, modifications and substitutions as fall within the true spirit and scope of the invention.

The following citations are referred to above in this disclosure, and each of these citations is incorporated by reference in its entirety: S. C. Srivastava, S. K. Raza, and R. Misra, Nucleic Acids Research, 1994, 22, 1296–304; M. E. Hawkins, W. Pfleiderer, O. Jungmann, and F. M. Balis, Analytical Biochemistry, 2001, 298, 231–240; M. E. Hawkins, W. Pfleiderer, F. M. Balis, D. Porter, and J. R. Knutson, Analytical Biochemistry, 1997, 244, 86–95; S. L. Driscoll, M. E. Hawkins, F. M. Balis, W. Pfleiderer, and W. R. Laws, Biophysical Journal, 1997, 73, 3277–86; R. Charubala, et al., Nucleoside Nucleotide, 1997, 16, 1369–1378; J. M. Jean and K. B. Hall, Proceedings of the National Academy of Sciences USA, 2001, 98, 37–41. J. Woo, R. B. Meyer, Jr., and H. B. Gamper, Nucleic Acids Research, 1996, 24, 2470–5; C. Liu and C. T. Martin, Journal of Molecular Biology, 2001, 308, 465–75; Landegren U., Kaiser, R., Caskey, C. T., Hood, L., Science, 1988, 242, 229–237; Prober et. al., Science, 1987, 238:336–341; Barrio, J. R., Secrist III, J. A., and Leonard, N. J., Biochemical & Biophysical Research Communications. 1972, 46, 597; Hawkins, M. E., Pfleiderer, W., Mazumder, A., Pommier, G., and Balis, F. M., Nucleic Acids Research, 1995, 23, 2872–2880; McGuigan et. al., Antiviral Chem. Chemother., 2000, 11, 343–348; Jpn Kokai JP 62059293, (1987); Nippon Kagaku Kaishi, 1987, 7, 1214–1220; Lund et al., J. Natl. Cancer Inst., 1994, 86, 1530–1533; Chabner, B. A., Cancer Chemotherapy: Principles and Practice, 2nd Ed., 1995, J. B. Lippincott Co., Philadelphia; Micklefield, J. Curr. Medicinal Chemistry, 2001, 8, 1157–1179; Freier, S M. and Altmann, K-H, Nucleic Acids Res., 1997, 25, 4429–43; Gryaznov, S M, Biochim Biophys. Acta, 1999, 1489, 131–40; Rait et al., Nucleosides Nucleotides, 1999, 18, 1379–80; Ray et al., FASEB J, 2000, 14, 1041–60; Braasch et al., Chem. Biol., 2001, 8, 1–7; Hasegawa et al., *Bioorg Med. Chem. Lett.,* 2002, 12, 73–6; Robins, et al., *J. Org. Chem.,* 1983, 48, 1854–1862; and McGuigan, C., et al., *J Med. Chem.* 1999, 42, 4479–4484; Ellington, A. D. and Szostak, J. W., *Nature,* 1990, 346, 818–822; Tuerk, C. and Gold, L. *Science,* 1990, 249, 505–510; Breaker, R. R. *Nat Biotechnol,* 1999, 17, 422–423; Joyce, G. F. *Proc Natl Acad Sci USA,* 1998, 95, 5845–5847; Reader, J. S., and Joyce, G. F. *Nature,* 2002, 420, 841–844.; James, B. D., Olsen, G. J., Liu, J. S., and Pace, N. R. *Cell,* 1988, 52, 19–26; Tarasow, T. M., Tarasow, S. L., and Eaton, B. E. *Nature,* 1997, 389, 54–57; Morris, K. N., Tarasow, T. M., Julin, C. M., Simons, S. L., Hilvert, D., and Gold, L. *Proc Natl Acad Sci USA,* 1994, 91, 13028–13032; Cairns, M. J., Hopkins, T. M., Witherington, C., Wang, L., and Sun, L. Q. *Nat. Biotechnol.,* 1999, 17, 480–486; Hesselberth, J., Robertson, M. P., Jhaveri, S., and Ellington, A. D. *J Biotechnol.,* 2000, 74, 15–25; Jhaveri, S., Rajendran, M., and Ellington, A. D. *Nat Biotechnol.,* 2000, 18, 1293–1297; and REF Sood, A., Shaw, B. R., Spielvogel, B.F., *J. Am. Chem. Soc.,* 112, 9000–9001, (1990).

What is claimed is:

1. A composition having formula (II):

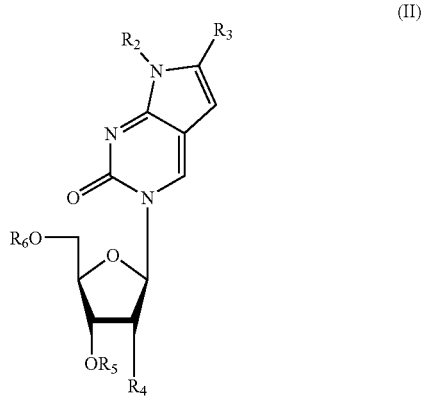

(II)

wherein $R_2$ is selected from the group consisting of hydrogen and an acetyl group;

$R_3$ is an alkyl having one to three carbons or allyl;

$R_4$ is selected from the group consisting of hydrogen, a hydroxyl group, a protected hydroxyl group, fluorine, an aminoalkoxy group, an aminoalkoxy group wherein the amino group bears a protecting group, and a methoxy group;

$R_5$ is selected from the group consisting of an alkoxy-N,N-dialkyaminophosphinyl group, a 2-cyanoethoxy-N,N-diisopropylaminophosphinyl group and a methoxy-N,N-diisopropylaminophosphinyl group; and $R_6$ is a protecting group removable under acidic, neutral, or photochemical conditions.

2. The composition of claim 1 wherein $R_2$ represents hydrogen or an acetyl group, $R_3$ represents a methyl group, $R_4$ represents hydrogen, a fluorine, an aminoalkoxy group, an aminoalkoxy group wherein the amino group bears a protecting group, a methoxy group, a tert-butyldimethylsilyloxy group, a triisopropylsilyloxymethoxy group, or a 1-(2-fluorophenyl)-4-methoxypiperidin-4-yloxy group, $R_5$ represents a 2-cyanoethoxy-N,N-diisopropylaminophosphinyl group or a methoxy-N,N-diisopropylaminophosphinyl group, and $R_6$ represents a dimethoxytrityl group.

3. A composition having the formula:

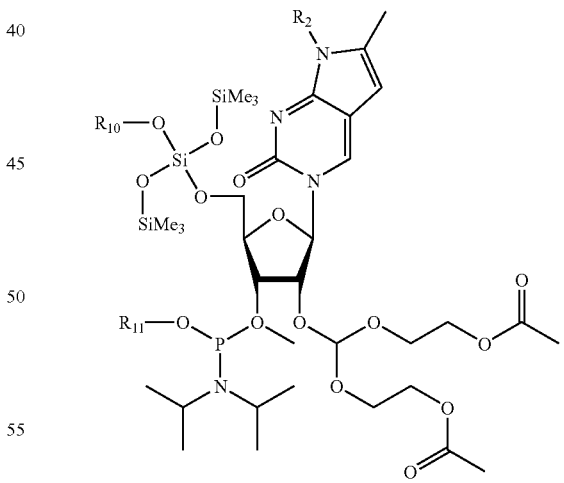

wherein $R_2$ represents hydrogen or acetyl group, $R_{10}$ represents a cyclooctyl, cyclododecyl, or diphenylmethyl group; and $R_{11}$ represents a 2-cyanoethyl or a methyl group.

* * * * *